US010092180B2

(12) United States Patent
Hart et al.

(10) Patent No.: US 10,092,180 B2
(45) Date of Patent: *Oct. 9, 2018

(54) OPTICAL COHERENCE TOMOGRAPHY (OCT) IMAGING SYSTEMS HAVING ADAPTABLE LENS SYSTEMS AND RELATED METHODS AND COMPUTER PROGRAM PRODUCTS

(71) Applicant: Bioptigen, Inc., Morrisville, NC (US)

(72) Inventors: Robert H. Hart, Cary, NC (US); Eric L. Buckland, Hickory, NC (US); Glenn A. Myers, Durham, NC (US); Joseph A. Izatt, Raleigh, NC (US); Joseph Elliott Vance, Durham, NC (US)

(73) Assignee: Bioptigen, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/810,939

(22) Filed: Nov. 13, 2017

(65) Prior Publication Data

US 2018/0084992 A1 Mar. 29, 2018

Related U.S. Application Data

(63) Continuation of application No. 15/464,568, filed on Mar. 21, 2017, now Pat. No. 9,814,383, which is a
(Continued)

(51) Int. Cl.
*A61B 3/14* (2006.01)
*A61B 3/10* (2006.01)
(Continued)

(52) U.S. Cl.
CPC ............ *A61B 3/102* (2013.01); *A61B 5/0066* (2013.01); *G02B 26/105* (2013.01); *A61B 5/0073* (2013.01)

(58) Field of Classification Search
CPC ........... A61B 3/102; A61B 3/103; A61B 3/12; A61B 3/1025; A61B 3/14; A61B 5/0066;
(Continued)

(56) References Cited

U.S. PATENT DOCUMENTS

| 5,186,173 A | 2/1993 | Zuckerman ................... 600/329 |
| 5,455,645 A | 10/1995 | Berger et al. ................. 351/223 |

(Continued)

FOREIGN PATENT DOCUMENTS

| WO | WO 2005080911 A1 | 9/2005 |
| WO | WO 2007/041125 A | 4/2007 |
| WO | WO 2007/041125 A1 | 4/2007 |

OTHER PUBLICATIONS

Partial International Search Report, International Application No. PCT/US2009/002535, dated Aug. 4, 2009.
(Continued)

*Primary Examiner* — Mahidere Sahle
(74) *Attorney, Agent, or Firm* — Ward and Smith, P.A.

(57) ABSTRACT

OCT imaging systems are provided for imaging a spherical-type eye including a source having an associated source arm path and a reference arm having an associated reference arm path coupled to the source path. The reference arm path has an associated reference arm path length. A sample is also provided having an associated sample arm path coupled to the source arm and reference arm paths. A lens having a focal power optimized for a diameter of the spherical-type eye is provided along with a reference arm path length adjustment module coupled to the reference arm. The reference arm path length adjustment module is configured to automatically adjust the reference arm path length such that the reference arm path length is based on an eye diameter of the subject.

10 Claims, 16 Drawing Sheets

Related U.S. Application Data continuation of application No. 14/301,670, filed on Jun. 11, 2014, now Pat. No. 9,622,658, which is a continuation of application No. 12/439,323, filed on Apr. 24, 2009, now Pat. No. 8,783,866.

(60) Provisional application No. 61/047,592, filed on Apr. 24, 2008.

(51) Int. Cl.
 *G02B 26/10* (2006.01)
 *A61B 5/00* (2006.01)

(58) Field of Classification Search
 CPC .............. A61B 5/0073; G01B 9/02091; G06T 2207/30041
 USPC ......................................................... 351/206
 See application file for complete search history.

(56) References Cited

U.S. PATENT DOCUMENTS

| | | | |
|---|---|---|---|
| 6,741,359 B2 | 5/2004 | Wei et al. | 356/512 |
| 7,072,047 B2 | 7/2006 | Westphal et al. | |
| 7,593,559 B2 | 9/2009 | Toth et al. | 382/128 |
| 2006/0066869 A1 | 3/2006 | Ueno et al. | 356/497 |
| 2006/0187462 A1 | 8/2006 | Srinivasan et al. | |
| 2007/0081166 A1 | 4/2007 | Brown et al. | 356/479 |
| 2007/0128662 A1 | 6/2007 | Isacoff et al. | 435/7.1 |
| 2007/0263226 A1 | 11/2007 | Kurtz et al. | |
| 2008/0007733 A1 | 1/2008 | Marks et al. | |
| 2008/0055543 A1 | 3/2008 | Meyer et al. | 351/205 |
| 2008/0074614 A1 | 3/2008 | Leblanc et al. | 351/205 |
| 2008/0231807 A1 | 9/2008 | Lacombe et al. | 351/215 |
| 2008/0291397 A1 | 11/2008 | Tesar | 351/221 |
| 2008/0309876 A1 | 12/2008 | Massie | 351/219 |
| 2009/0103050 A1 | 4/2009 | Michaels et al. | 351/208 |
| 2010/0321636 A1 | 12/2010 | Buckland et al. | 351/206 |
| 2015/0297084 A1 | 10/2015 | Boppart | A61B 5/0066 600/425 |

OTHER PUBLICATIONS

International Search Report and Written Opinion corresponding to International Application No. PCT/US2009/002535; dated Nov. 6, 2009.

International Preliminary Report on Patentability corresponding to International Application No. PCT/US2009/002535; dated Nov. 4, 2010.

Ruggeri et al. "In Vivo Three-Dimensional High-Resolution Imaging of Rodent Retina with Spectral-Domain Optical Coherence Tomography," Investigative Ophthalmology & Visual Science, Apr. 2007, vol. 48, No. 4, pp. 1808-1814.

Srinivasan et al. "Noninvasive Volumetric Imaging and Morphometry of the Rodent Retina with High-Speed, Ultrahigh-Resolution Optical Coherence Tomography," Investigative Ophthalmology & Visual Science, Dec. 2006, vol. 47, No. 12, pp. 5522-5628.

"Eyeball", Merriam-Webster.com, Web, Jul. 25, 2016.

Position B: far

Position A: near

0 Diopter

20 Diopter

80 Diopter

80 Diopter objective using quad doublets

Imaging of retina with 80 D quad doublets

Focus on Cornea

Focus on Retina

Telecentric imaging optic

Working Position A: Cornea

Working Position B: Anterior Lens

Working Position C: Posterior Lens

Working Position D: Retina

Center focused on posterior cornea surface

Center focused on anterior cornea surface

Optimum position depth for best lateral resolution across field of view

| Surface# | Curvature | Thickness | Glass | Semi-Diameter | Conic |
| --- | --- | --- | --- | --- | --- |
| 0 | 0.000 | 0.00 | | 0.00 | 0.00 |
| 1 | 0.000 | 8.02 | | 0.00 | 0.00 |
| 2 | 0.000 | 5.00 | C0550 | 2.75 | 0.00 |
| 3 | -0.151 | 26.30 | | 2.75 | -0.55 |
| 4 | 0.000 | 0.00 | | 0.00 | 0.00 |
| 5 | 0.000 | 0.00 | | 0.00 | 0.00 |
| 6 | 0.000 | 0.00 | MIRROR | 3.00 | 0.00 |
| 7 | 0.000 | 0.00 | | 0.00 | 0.00 |
| 8 | 0.000 | -50.00 | | 0.00 | 0.00 |
| 9 | -0.004 | -1.50 | SFL6 | 12.70 | 0.00 |
| 10 | -0.019 | -4.00 | LAKN22 | 12.70 | 0.00 |
| 11 | 0.015 | -1.00 | | 12.70 | 0.00 |
| 12 | -0.015 | -4.00 | LAKN22 | 12.70 | 0.00 |
| 13 | 0.019 | -1.50 | SFL6 | 12.70 | 0.00 |
| 14 | 0.004 | 0.00 | | 12.70 | 0.00 |
| 15 | 0.000 | -65.40 | | 7.60 | 0.00 |
| 16 | -0.015 | -2.00 | SFL6 | 6.35 | 0.00 |
| 17 | -0.075 | -5.00 | LAKN22 | 6.35 | 0.00 |
| 18 | 0.062 | -1.00 | | 6.35 | 0.00 |
| 19 | -0.062 | -5.00 | LAKN22 | 6.35 | 0.00 |
| 20 | 0.075 | -2.00 | SFL6 | 6.35 | 0.00 |
| 21 | 0.015 | 0.00 | | 6.35 | 0.00 |
| 22 | 0.000 | -5.40 | | 0.62 | 0.00 |
| 23 | 0.141 | 0.00 | | 0.92 | 0.00 |
| 24 | -0.659 | -0.09 | CORNEA,MOUSE | 1.52 | 0.00 |
| 25 | -0.684 | -0.45 | AQUEOUS,MOUSE | 1.46 | 0.00 |
| 26 | -0.801 | -2.03 | LENS,MOUSE | 1.19 | 0.00 |
| 27 | 0.866 | -0.56 | VITREOUS, MOUSE | 1.16 | 0.00 |
| 28 | 0.609 | 0.00 | | 1.64 | 0.00 |

Figure 16

OPTICAL COHERENCE TOMOGRAPHY (OCT) IMAGING SYSTEMS HAVING ADAPTABLE LENS SYSTEMS AND RELATED METHODS AND COMPUTER PROGRAM PRODUCTS

CLAIM OF PRIORITY

The present application is a continuation of U.S. patent application Ser. No. 15/464,568, filed Mar. 21, 2017, which is a continuation of U.S. patent application Ser. No. 14/301,670, filed Jun. 11, 2014 (now U.S. Pat. No. 9,814,383), which is continuation of U.S. patent application Ser. No. 12/429,323, filed Apr. 24, 2009 (now U.S. Pat. No. 8,783,866), which claims priority from U.S. Provisional Application No. 61/047,592, filed Apr. 24, 2008, the disclosures of which are hereby incorporated herein by reference as if set forth in their entireties.

STATEMENT OF GOVERNMENT SUPPORT

This invention was made with government support under grant number 2R44EY015585 awarded by National Institutes of Health, National Eye Institute. The United States Government has certain rights in this invention.

FIELD

The present invention relates to imaging and, more particularly, to optical coherence tomography (OCT) and related systems, methods and computer program products.

BACKGROUND

Spectral Domain (SD)-OCT provides real time images of surface and subsurface structures. In the eye, for example, OCT can be used to image the cornea, the iris, the crystalline lens and the retina. Typically, the subject being imaged is a cooperative adult patient having their head positioned in a chin-rest before imaging the eye. The imaging optics used are typically optimized for the human adult eye, and specifically for imaging of the anterior segment of the eye, i.e., the cornea to the iris, or the posterior pole of the eye, i.e., the retina. In conventional systems, these distinct portions of the eye require independent optical imaging systems, and generally cannot be imaged using the same optics. Furthermore, such systems are now commonly configured with an iris camera, a fundus camera, or a scanning laser ophthalmoscope (SLO) or line scanning ophthalmoscope (LSO), that provide high speed photographic views of the respective features of the eye to facilitate alignment of the OCT image, and a record of the location of the OCT image.

Not all subjects of interest are cooperative as the adult patient. Furthermore, not all subjects of interest have optical properties that are similar or equivalent to the adult eye, or are even scaled versions of the adult eye. For example, a rodent eye more closely approximates a spherical, or ball, lens. Imaging the retina of the rodent eye, for either fundus photography, SLO or LSO imaging, or OCT, typically requires objective optics specifically designed for these ball-lens systems. Rodents are in an important class of subjects for pre-clinical research that cannot be imaged in a typical clinical imaging appliance for many reasons. For example, most rodents do not cooperate with chin-rest alignment systems. Yet rodent imaging is very important for research in ophthalmology and in research of systemic disease processes that influence neurologic and vascular function. Rodents, for example, mice and rats, are very well suited models for evaluating biological function as wild-type, are well suited to genetic modification for evaluating specific genotypes and phenotypes, and provide excellent models for evaluating response to a wide variety of treatments. Accordingly, high resolution, high throughput imaging systems that provide the highest quality images of ocular structure in rodent models efficiently and reproducibly may be desired.

SUMMARY

Some embodiments of the present invention provide optical coherence tomography (OCT) systems for imaging an eye including a lens system configured to adjust such that the lens system can image both anterior and posterior regions of the eye without changing any lenses in the lens system.

In further embodiments of the present invention, the lens system may include three lens complexes, each of the lens complexes including at least one lens. The lens system may include first, second and third lenses. The first lens may be a collimator lens and have a focal length of f1; a distance D1A distal to the collimator lens may be a galvanometer configured to steer a light beam over a region of interest in the eye; the second lens may be a distance D1B distal from the galvanometer and have a focal length f2; and a distance D2A distal to the second lens may be a plane perpendicular to an optical axis dividing a distance D2 into two parts, the distance D2A and a distance D2B.

In still further embodiments of the present invention, the distance D1B and the distance D2A are approximately equal to the focal length f2 and the distance D2B is variable. In certain embodiments, the distance D1A is adjustable. The third lens may be an objective lens, has a focal length f3 and may be the variable distance D2B to the right of the plane.

In some embodiments, the system may further include a distance D_cornea from the objective lens to an anterior surface of the cornea; a distance D_pivot to a pivot point at a point optically conjugate to a position of the galvanometer, where scanning beams cross; and a distance D_focus in air where the optical beams are in focus. D_pivot may be approximately equal to the focal length f3 beyond the objective lens and wherein distance D_focus may be determined by the following lens formula: $1/D2B + 1/D\_focus = 1/f3$, wherein the index of refraction of a media in which D2B and D_focus reside is approximately equal to 1.

In further embodiments of the present invention, the lens system may have a first configuration wherein the probe bore tip containing the objective lens is extended to increase the distance D2B to a threshold value. The threshold value may be determined using the lens formula to place a distance D_focus at a proper distance from the objective lens for imaging the cornea and to optimize a depth of focus to a desired value for imaging the cornea.

In still further embodiments of the present invention, the lens system may have a second configuration wherein a handheld probe of the OCT system and the lens system is driven closer to the eye and wherein an operator of the handheld probe slowly draws the probe bore tip toward a nominal lens position, which shortens the distance D2B, lengthens a distance D_focus and keeps a distance D_pivot constant. The distance D2B may be between f3 and 2*f3 such that an anterior segment of the eye provides a portion of optical power used to focus an optical beam on intermediate structures of the eye.

In some embodiments of the present invention, the lens system may have a third configuration where a handheld probe of the OCT system is moved closer to the eye and an operator of the probe contracts the probe bore tip back to a nominal retina position, which occurs when D2B=f3 and continues moving the probe inward until a distance D_cornea is approximately equal to a design working distance to the eye and a distance D_pivot places a pivot point in an iris plane.

In further embodiments of the present invention, a reference arm path length of the OCT system may be adjusted to accommodate subject eye lengths in a sample arm of the OCT system.

In still further embodiments of the present invention, a reference arm path length of the OCT system may be adjusted to accommodate subject path lengths to target structures within the eye, target structures ranging from anterior of the cornea to posterior of the retina. Anterior to posterior structures of a spherical-type sample are imaged continuously by synchronous coordination of a working distance between an objective lens and an anterior surface of the sample, and the reference arm path length. The continuous anterior to posterior imaging may be accomplished automatically using a data processing system, wherein the relationship between working distance and the reference arm path length is determined by a pre-defined function or look-up table.

In some embodiments of the present invention, the lens system may have an associated focus adjustment that enables the OCT system to be focused based on refractive correction.

In further embodiments of the present invention, the system may be a wide field imaging system providing a field of view of about equal to or greater than 50 degrees.

In still further embodiments of the present invention, the system may be a wide field imaging system providing a field of view of about equal to or greater than 140 degrees in combination with rotation about a pupil.

In some embodiments of the present invention, the OCT system may be portable such that the OCT system is provided to the subject where the subject is located. The portable OCT system may be configured to provide imaging to a subject independent of the orientation of the subject. The portable OCT system may include a video and/or digital fundus camera.

In further embodiments of the present invention, the portable OCT system may further include a foot pedal and/or finger trigger configured to control focus adjustment, reference arm path length adjustment and/or trigger acquisition of an image.

Still further embodiments of the present invention provided optical OCT imaging systems for imaging an eye, including optics configured to image an eye having a spherical shape.

In some embodiments of the present invention, an amount of optical power used to obtain an OCT image of the eye having a spherical shape is a function of a spherical radius of the eye. The eye may be a rodent eye.

In further embodiments of the present invention, the system further comprises a telecentric lens that is a doublet pair configured to create a telecentric plane with a substantially flattened field curvature at the telecentric plane. The doublet pair may yield a telecentric plane having a field curvature radius of greater than about 100 mm.

In still further embodiments of the present invention, the system may further include a focusing lens set configured to have substantially greater power to accommodate the spherical shaped eye. Power for a mouse may be about +80 D and power for a rat having an eye diameter of about 6.4 mm may be about 73 Diopters.

Some embodiments of the present invention provide methods for imaging an in eye using OCT system including imaging both anterior and posterior regions of the eye without changing any lenses in the lens system.

Further embodiments of the present invention provide methods for imaging an eye in an OCT imaging system including imaging an eye having a spherical shape using optics configured to image spherical shaped objects.

Still further embodiments of the present invention provide methods for imaging an eye in an OCT imaging system including imaging continuously from an anterior position of the eye to a posterior position of the eye by synchronous coordination of a working distance between a lens and a sample and a reference arm path length.

Some embodiments of the present invention provide computer program products for imaging in an eye using OCT systems including computer readable storage medium having computer readable program code embodied in said medium. The computer readable program code including computer readable program code configured to image both anterior and posterior regions of the eye without changing any lenses in the lens system.

Further embodiments of the present invention provide computer program products for imaging in an eye using OCT systems including computer readable storage medium having computer readable program code embodied in said medium. The computer readable program code including computer readable program code configured to image an eye having a spherical shape using optics configured to image spherical shaped objects.

Still further embodiments of the present invention provide OCT imaging systems for imaging a spherical-type eye including a source having an associated source arm path; a reference arm having an associated reference arm path coupled to the source path, the reference arm path having an associated reference arm path length; a sample having an associated sample arm path coupled to the source arm and reference arm paths; a lens having a focal power optimized for a diameter of the spherical-type eye; and a reference arm path length adjustment module coupled to the reference arm, the reference arm path length adjustment module configured to automatically adjust the reference arm path length such that the reference arm path length is based on an eye diameter of the subject.

In some embodiments of the present invention the reference arm path length is adjusted to accommodate subject eye diameters in the sample arm ranging from about 1.0 mm to about 15 mm.

In further embodiments of the present invention, a lens system including at least one lens is provided in the sample arm path and at least one surface of the eye, the lens system having a field curvature that matches a curvature of a retina of the spherical eye of the subject.

In still further embodiments of the present invention, the subject may be a mouse, a rat or a macaque.

Some embodiments of the present invention provide optical imaging lenses for imaging a back surface of a ball-lens subject or ball-lens type eye including an achromatic doublet pair; and an optical power determined from a function or table and corresponding to a diameter or curvature of subject surfaces, wherein the optical power is greater than or equal to +30 D.

BRIEF DESCRIPTION OF THE DRAWINGS

FIG. 16 a table illustrating design prescription for mouse retinal imaging corresponding to the lens system of FIG. 8 and the mouse eye model of FIG. 9 in accordance with some embodiments of the present invention.

DETAILED DESCRIPTION OF EMBODIMENTS OF THE INVENTION

Figure 1:
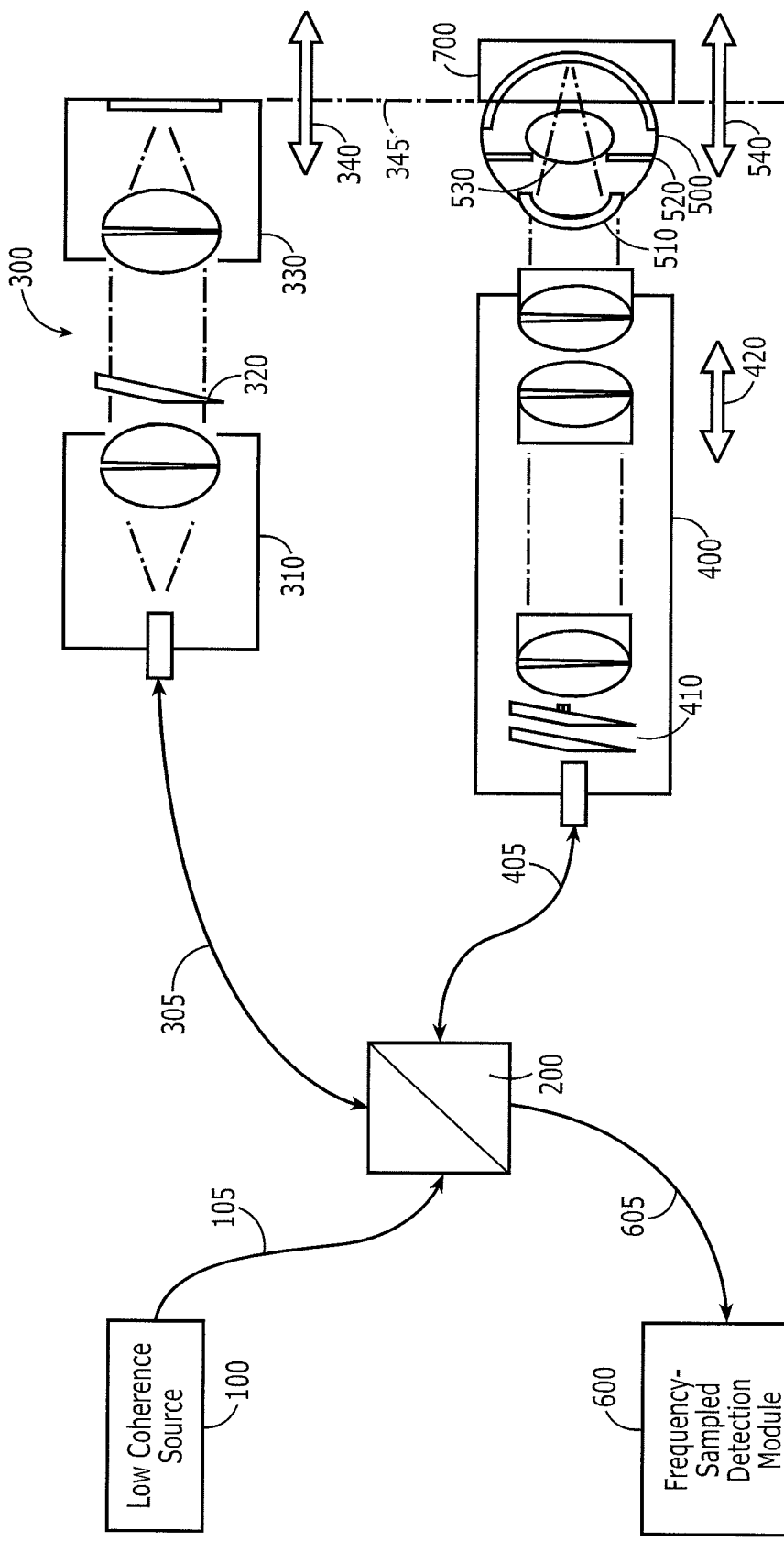
FIG. 1 is a block diagram illustrating a Fourier domain retinal optical coherence tomography system in accordance with some embodiments of the present invention.

The present invention will be described more fully hereinafter with reference to the accompanying figures, in which embodiments of the invention are shown. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

Conventional imaging systems do not provide high quality images of spherical eyes found in, for example, rodents. As discussed above, the capability of imaging spherical rodent eyes may be very important to clinical research. Accordingly, some embodiments of the present invention provide imaging systems that provide high quality imaging of posterior imaging structures of animal models with ball-lens ocular phenotypes. In some embodiments, these imaging systems of allow imaging of both anterior structures and posterior structures of the eye without changing the imaging lenses in the system.

In some embodiments of the present invention, imaging systems are configured to provide a continuous view of structures from the anterior of the cornea through the posterior, or outer layers, of the retina to the extent of optical translucency, as a simple function of relative position of the imaging lens to the eye of the subject, for example, by changing the working distance.

In some embodiments of the present invention, the imaging system can be applied to photographic, SLO or LSO, or OCT images of the structures of the subject model.

In some embodiments of the present invention, an optical prescription is provided for this optical system that provides for optimal lateral resolution in the imaging of the posterior pole of the subject eye.

In some embodiments of the present invention, an optical prescription is provided for this optical system that provides for optimal matching between the field curvature of the focal plane at the retina of the subject eye with the curvature of the retina of the subject.

In some embodiments of the present invention, an optical prescription is provided for this optical system that provides for optimal imaging of the retina of a subject having a ball-lens phenotype, whereby the prescription scales with the diameter of the subject eye.

In some embodiments of the present invention, a prescription for alignment and imaging of these subject models is provided that includes observing an image acquired as the imaging lens is brought into increasingly close proximity to the subject eye by observing orientation of the structural features of the subject eye as a function of depth.

In some embodiments of the present invention, a prescription is provided for alignment and imaging of these subject models that includes modifying alignment of the optical system in response to feedback from the observation of the image acquired as the imaging lens is brought into increasingly close proximity to the subject eye by observing orientation of the structural features of the subject eye as a function of depth.

In some embodiments of the present invention, a prescription for optimizing the quality and performance of an OCT imaging system is provided by adjusting the reference arm length in coordination with the sample arm length of the interferometric imaging system in a continuous manner as the imaging system is positioned for imaging structures from the anterior of the cornea through to the posterior of the retina.

In some embodiments of the present invention the OCT imaging of arbitrary structures through a ball-lens optic is provided.

The adult human eye is a very capable imaging system. The emmetropic human eye focuses distant objects at the retina, using the refractive power of the cornea and the ocular lens. Close subjects are focused on the retina by accommodation of the lens, a process that may degrade with age, i.e. presbyopia. The typical human subject requires some degree of external correction for imperfect refractive properties of the eye. A myopic, or near-sighted, subject, tends to focus distant objects in front of the retina, and corrective lenses with negative optical power, is required for normal vision. Conversely, a hyperopic, or far-sighted, subject tends to focus distant objects behind the retina, and may require corrective lenses with positive power for normal vision. Imaging systems that image the retina therefore generally are designed to image the emmetropic human eye, with a range of focal corrections from +12 Diopter to −12 Diopter, and up to +/−20 Diopters.

Referring now to FIG. 1, a block diagram illustrating a Fourier domain retinal OCT system in accordance with some embodiments of the present invention will be discussed. As illustrated in FIG. 1, the system includes a low coherence source 100, a reference arm 300 and a sample arm 400 coupled to each other by a beamsplitter 200. The beamsplitter 200 may be, for example, a fiber optic coupler or a bulk or micro-optic coupler without departing from the scope of the present invention. In some embodiments, the beamsplitter 200 may provide from about a 50/50 to about a 90/10 split ratio. As further illustrated in FIG. 1, the beamsplitter 200 is also coupled to a frequency sampled detection module 600 over a path 605 that may be provided by an optical fiber.

As further illustrated in FIG. 1, the source 100 is coupled to the beamsplitter 200 by a source path 105. The source 100 may be, for example, an SLED or tunable source. The reference arm 300 is coupled to the beamsplitter over a reference arm path 305. Similarly, the sample arm 400 is coupled to the beamsplitter 200 over the sample arm path 405. In some embodiments of the present invention, the source path, the reference arm path and the sample arm path may all be provided by optical fiber.

In accordance with some embodiment of the present invention, the reference arm 300 further includes a collimator assembly 310, a variable attenuator 320 that can be neutral density or variable aperture, a mirror assembly 330, a reference arm variable path length adjustment 340 and a path length matching position 345, i.e. optical path length reference to sample. As further illustrated, the sample arm 400 according to some embodiments of the present invention may include a dual-axis scanner assembly 410 and an objective lens variable focus 420.

The sample in FIG. 1 is an eye 500 including a cornea 510, iris/pupil 520, ocular lens 530 and eye length 540. As will be discussed in detail herein, the eye length in accordance with some embodiments of the present invention may be a subject specific, age dependent, pathology dependent axial optical eye length. As further illustrated in FIG. 1, a representation of an OCT imaging window 700 is illustrated near the eye 500. As will be discussed further below, the retinal imaging system relies in the optics of the subject eye 500 to image the posterior structures of the eye.

Figure 2:
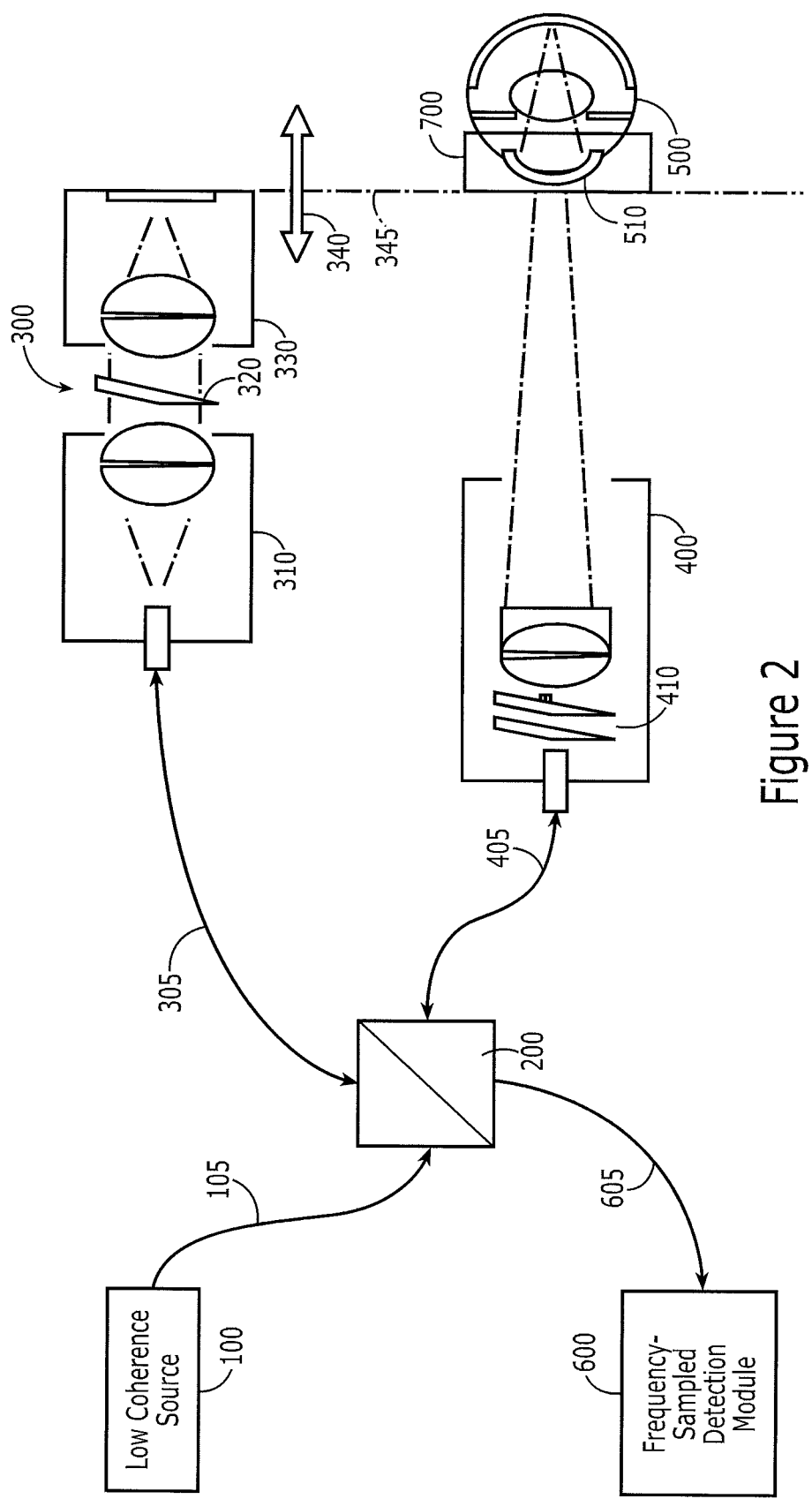
FIG. 2 is a block diagram illustrating a Fourier domain corneal optical coherence tomography system in accordance with some embodiments of the present invention.

FIG. 2 is a block diagram illustrating a Fourier domain (FD) cornea OCT system in accordance with some embodiments of the present invention. As illustrated therein, the system of FIG. 2 is very similar to the system of FIG. 1. However, the objective lens variable focus is not included. The anterior imaging system of FIG. 2 images the anterior structures directly, without reliance on the optics of the subject to focus on the anterior structures.

It will be understood that the refractive properties of the subject eye do impact the imaging, and such refractive properties may be accounted for in quantitative image correction as discussed in U.S. Pat. No. 7,072,047 to Westphal et al. Furthermore, imaging of intermediate structures, including the ocular lens, may be accomplished with appropriately designed optics. In many cases, interference, and thus imaging, is achieved in FDOCT image systems over a range of depths defined by an optical path-length matched condition between a reference reflection and backscattering from structures in the sample, bound by the ability to resolve high frequency components in a resultant spectral interferogram. Imaging conditions for FDOCT, including spectrometer-based (SDOCT) and swept-source-based configurations, are well known in the art.

Figure 3:
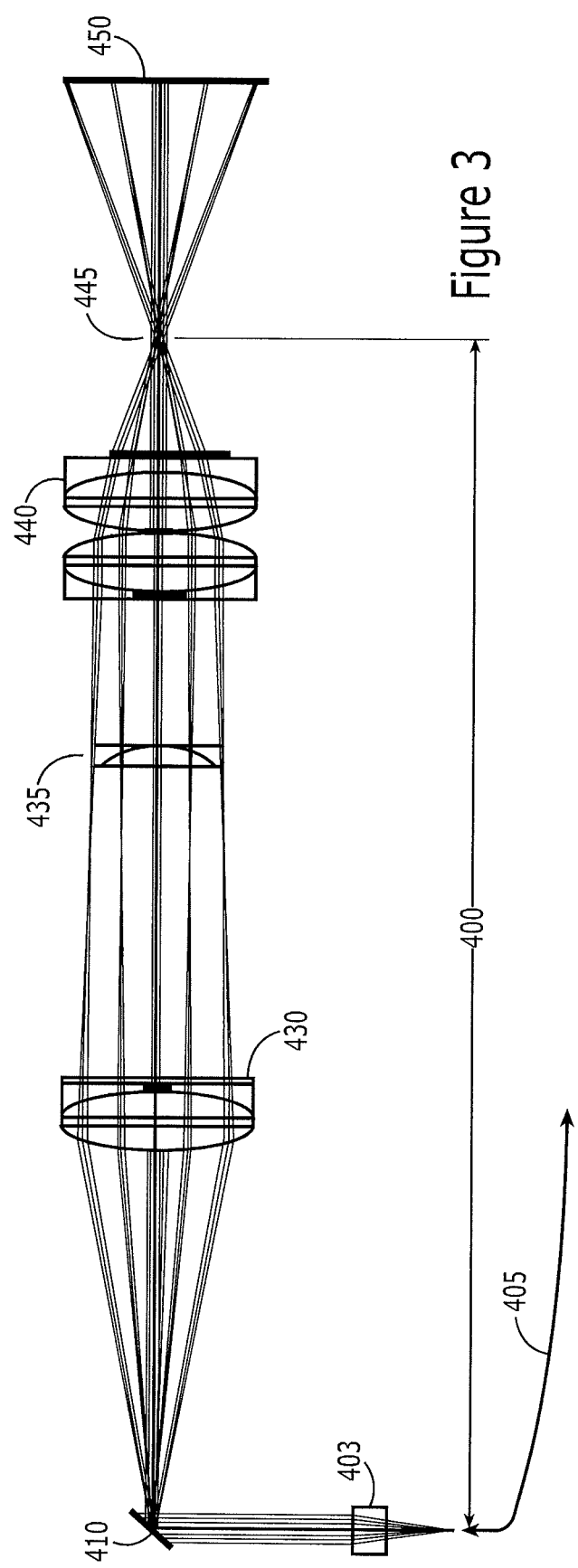
FIG. 3 is a diagram illustrating an optical system for human retinal imaging in accordance with some embodiments of the present invention.

Referring now to FIG. 3, a diagram illustrating a representative imaging system for adult human retinal OCT will be discussed. A sample arm signal is transferred by optical fiber to the scanning imaging system 400. The scanning imaging system may include the sample arm 400 and scanner assembly. The broadband light from the fiber is collimated 403, delivered to a 2-axis galvometric scanning system 410 (dual-axis scanner assembly), and imaged to telecentric imaging plane 435 with lens doublet 430. The telecentric imaging plane 435 has a field radius of curvature, for example, of 16 mm, and is a conjugate to the input optical fiber. The scanning system sweeps a beam across this telecentric plane, which is subsequently imaged to the retina using objective lens set 440 (lens doublet pair) and the optics of the eye. An important attribute of the retinal imaging system is the existence of a pivot point 445 that is conjugate to galvometric scanners. At the pivot plane 445, the telecentric scanning at 435 is converted into a sweeping scan that maps of a field of view of the retina. Vignette-free imaging is achieved by locating the pivot point 445 nominally within the pupil of the subject eye. A well-design imaging system can image without dilation of the eye, though dilation reduces sensitivity to the placement of the pivot point, a key aspect to accurate subject position and thus image quality. In the emmetropic imaging condition, the scanned rays that are the image of the input fiber at plane 435 are collimated by the lens set 440. The beams do not focus, but sweep out an angular pattern in the far field 450, pivoting around the galvo conjugate point 445. The far field 450 may be a radial-telecentric image plane, which is conjugate to the telecentric image plane 435 and has a field radius of curvature in air of about 7.1 mm. Optical power can be added or subtracted to correct for hyperopia or myopia by modifying the separation of the lenses in the lens set 440.

Figure 4B:
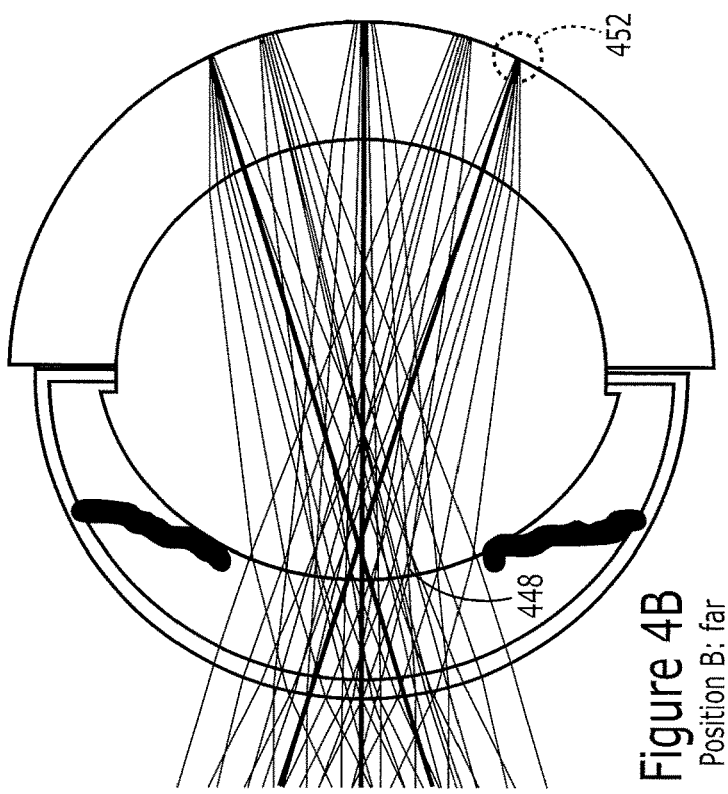
FIGS. 4A and 4B are diagrams illustrating focal conditions at a posterior pole of spherical eye in accordance with some embodiments of the present invention.
Figure 4A:
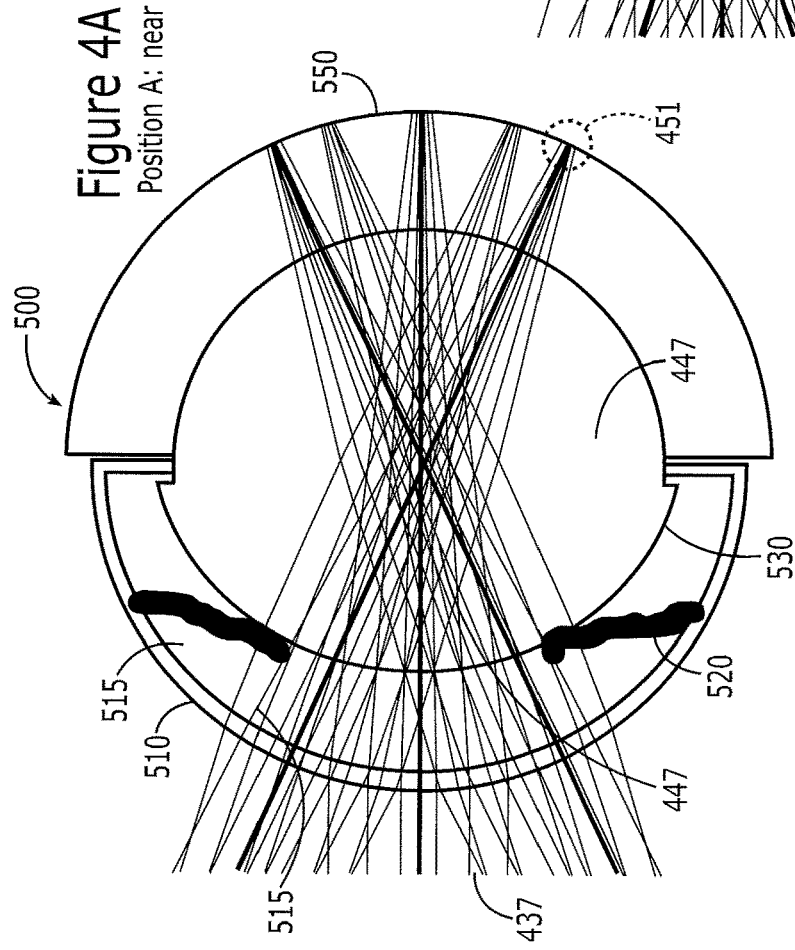

Referring now to FIGS. 4A and 4B, diagrams illustrating focal condition at posterior pole of a spherical eye, such as a mouse eye, in accordance with some embodiments of the present invention will be discussed. The imaging in FIG. 4 was modeled using human optimized optics as in FIG. 3, with emmetropic (zero Diopter) correction, shown as a function of working distance between the lens 440 and the cornea 510 of the rodent eye. The rodent eye is not well modeled as a scaled version of the human eye. The rodent eye is very nearly a spherical, or ball lens as illustrated in FIGS. 4A and 4B. The rodent eye 500 has similar structures to the human eye, including cornea 510, vitreous humor 515, pupil 520, lens 530, and retina 550. However, the shape of the cornea 510 and lens 530 are much more spherical. FIGS. 4A and 4B illustrate the capability of the emmotropic adult human optics illustrated in FIG. 3 to image the rodent eye (spherical eye) of FIG. 4. The diagrams of FIG. 4 actually model the eye of a mouse having a diameter of 3.2 mm. FIG. 4A illustrates the bundle of scanned rays 437 imaged to the retina with the pivot point 447 positioned within the pupil 520. The rays 451 are unable to focus at the retina. On a human eye, the on-axis rms spot size for the emmetropic subject is about 4.5 µm. In the mouse model, the spot size with these optics is 39 µm. Improvement might be anticipated by increasing the working distance between objective optics and subject, thus, moving the pivot point outward. However, the spot size only improves to about 38.8 µm, and the field of view is constrained. Vignetting becomes a significant problem. This problem is not adequately addressed by adding focusing power to the adult-optimized optics.

Figure 5A:
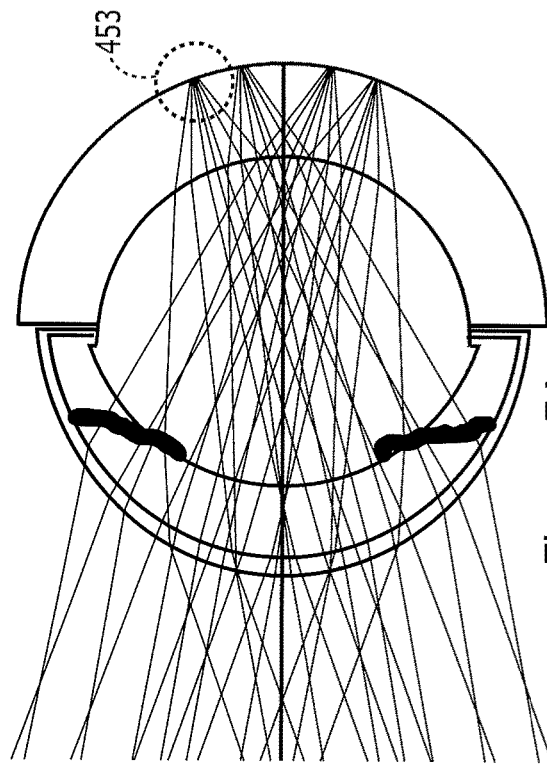
FIGS. 5A through 5C are diagrams illustrating focal conditions at posterior pole of spherical eye in accordance with some embodiments of the present invention.
Figure 5B:
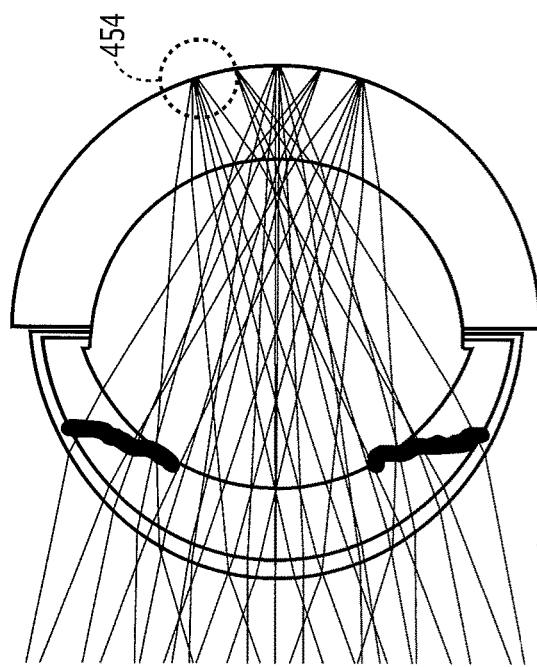
Figure 5C:
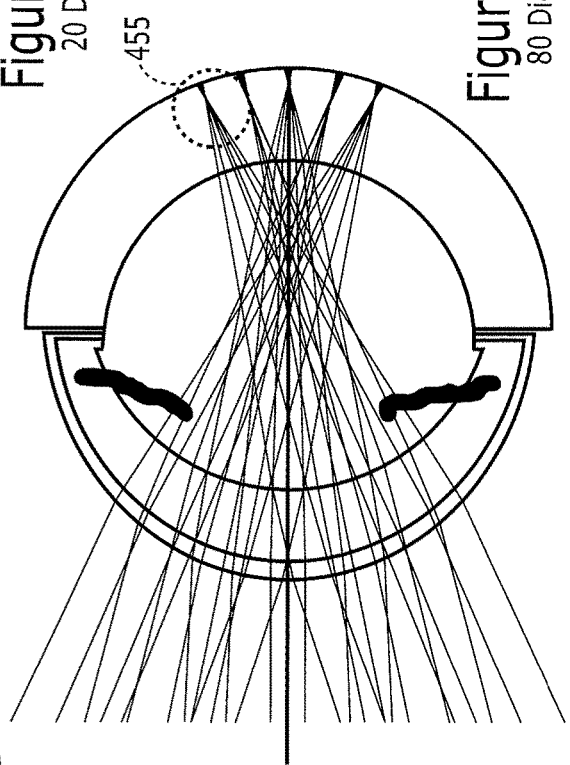

As illustrated in FIG. 5 the focusing on the rodent retina is not substantially improved by increasing the optical power of the of the human-optimized objective lens from 0 Diopter illustrated in FIG. 5A, to +20 Diopter illustrated in FIG. 5B (the extent of typical clinical retinal OCT systems), or to +80 Diopter illustrated in FIG. 5C. As the power is increased, the ball-lens optics makes it impossible to image the adult-optimized optics onto the retinal surface. Representative focal points are highlighted as structures 453, 454 and 455, respectively.

Figures 6A, 6B:
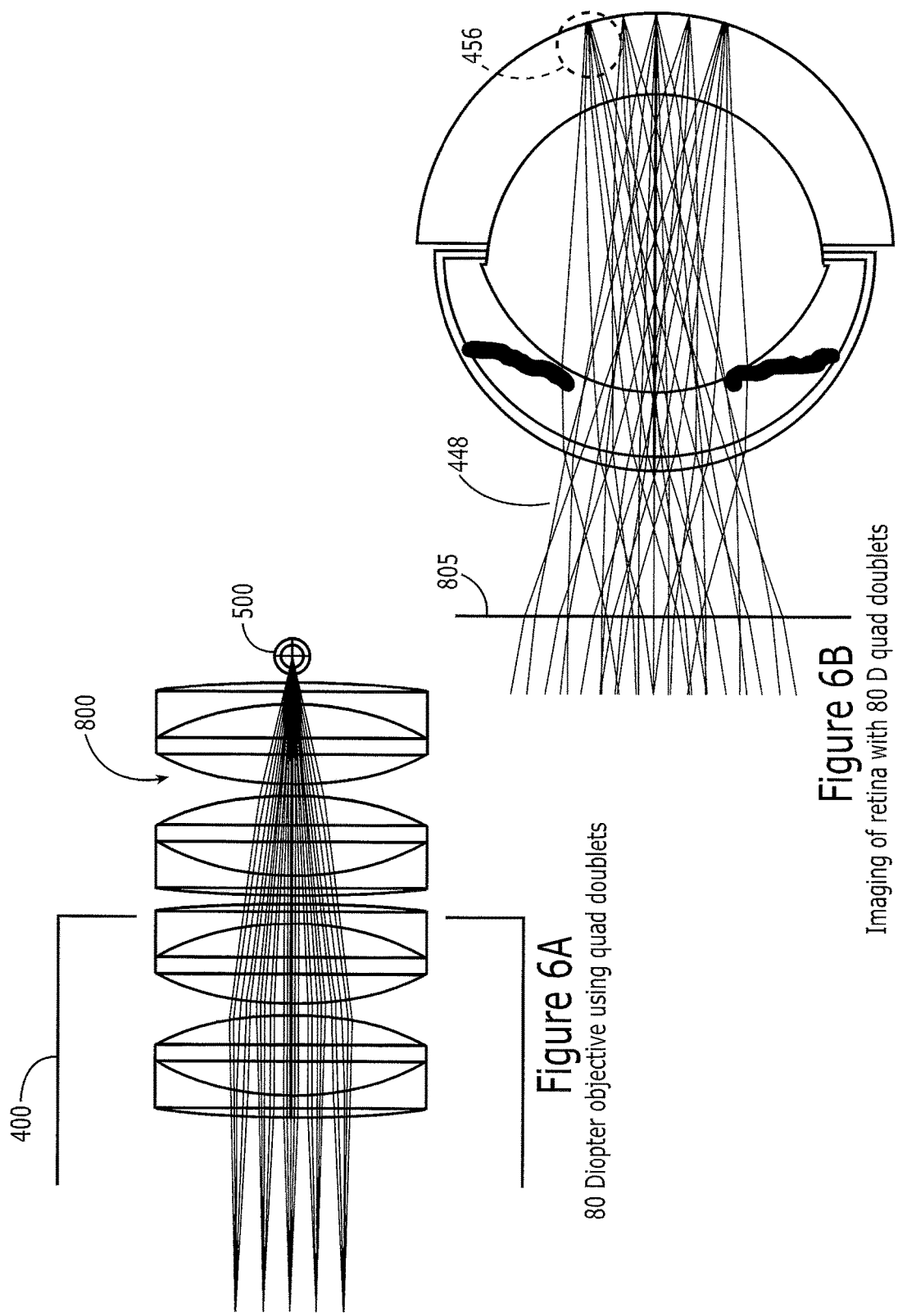
FIGS. 6A and 6B are diagrams illustrating images of a rodent retina with adult human optimized optics with an additional positive power doublet pair in accordance with some embodiments of the present invention.

In practice, it has been shown that some improvement can be achieved by adding an additional high power focusing optics between the adult imaging lens and the subject eye as illustrated, for example, in FIG. 6A. An optimized auxiliary doublet pair 800 improves focusing on the retina, yielding an on-axis rms spot of about 2.0 µm. However, the pivot point is substantially broadened into a pivot area 448, cannot be driven into the pupil, and the field of view is highly constrained, as demonstrated by the RMS Spot Diameter vs. Field of View graph illustrated in FIG. 12. This solution is, however, much better than the use of a single achromat solution most commonly applied. The single achromat yields an on axis rms spot of about 30 µm.

Figure 7B:
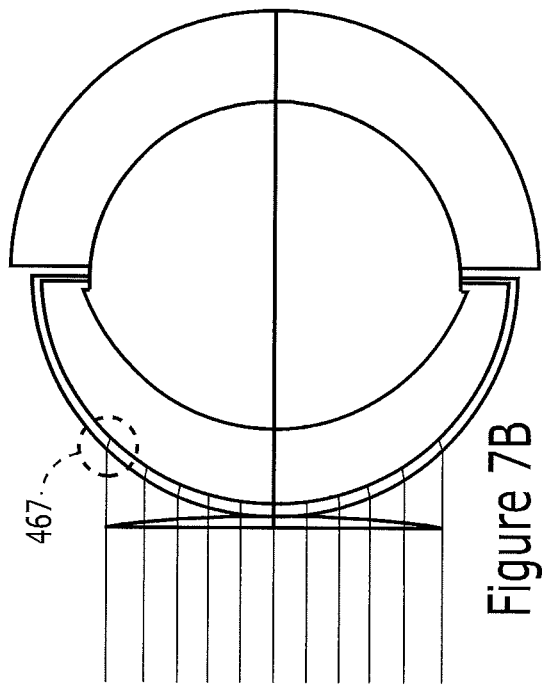
FIGS. 7A through 7C are diagrams illustrating imaging of an eye with typical telecentric cornea imaging optics in accordance with some embodiments of the present invention.
Figure 7C:
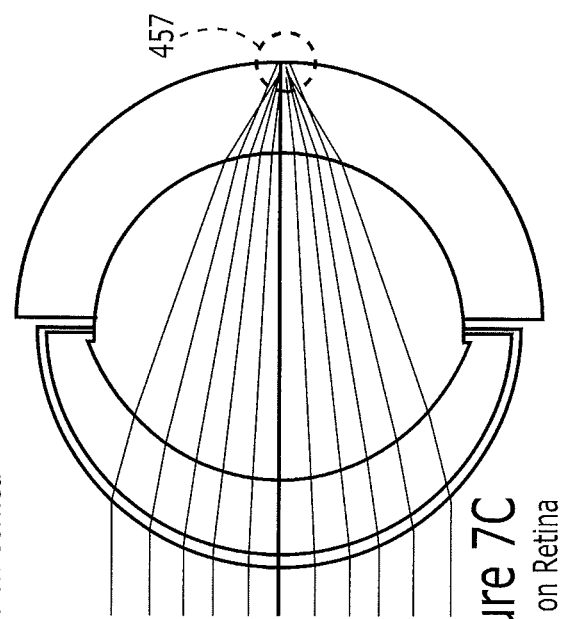
Figure 7A:
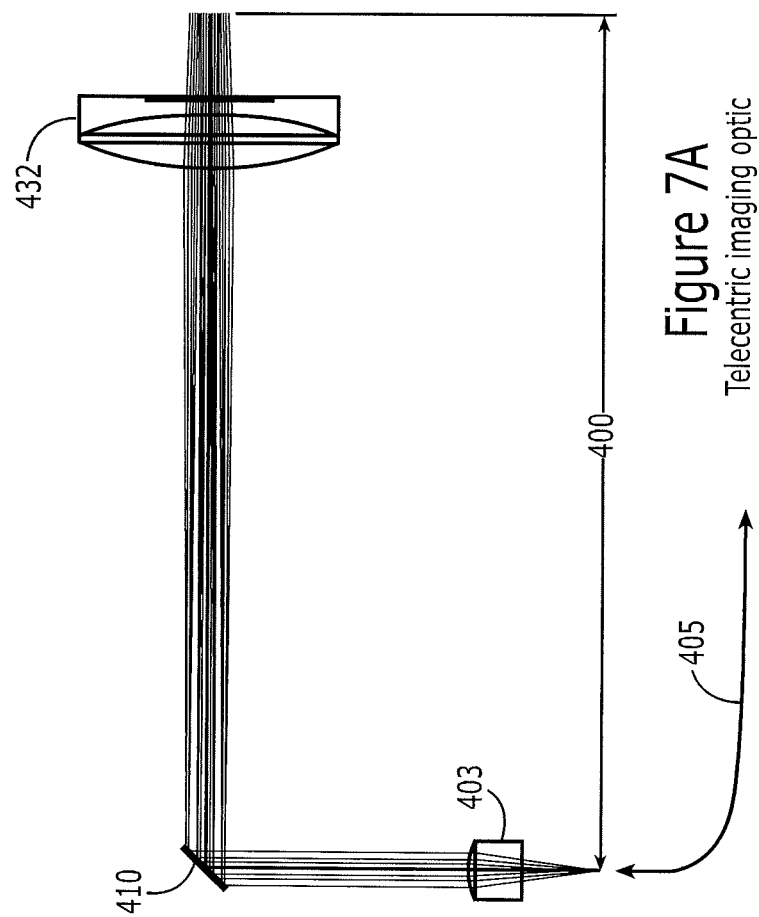

It will be understood that an anterior imaging lens, and specifically a cornea imaging lens, is nominally subject independent. A representative anterior imaging optic is shown in FIG. 7A. A simple doublet 432 scans telecentrically and focus at a prescribed working distance. The cornea can be imaged by placing the cornea at the appropriate focal working distance as shown in FIG. 7B. The rays 467 can focus anywhere in the cornea by adjusting the working distance, and the reference arm position to maintain appropriate path-matching. This optic cannot image the retina, as all scanned rays focus in on one broad spot 457 as seen in FIG. 7C.

Figure 8:
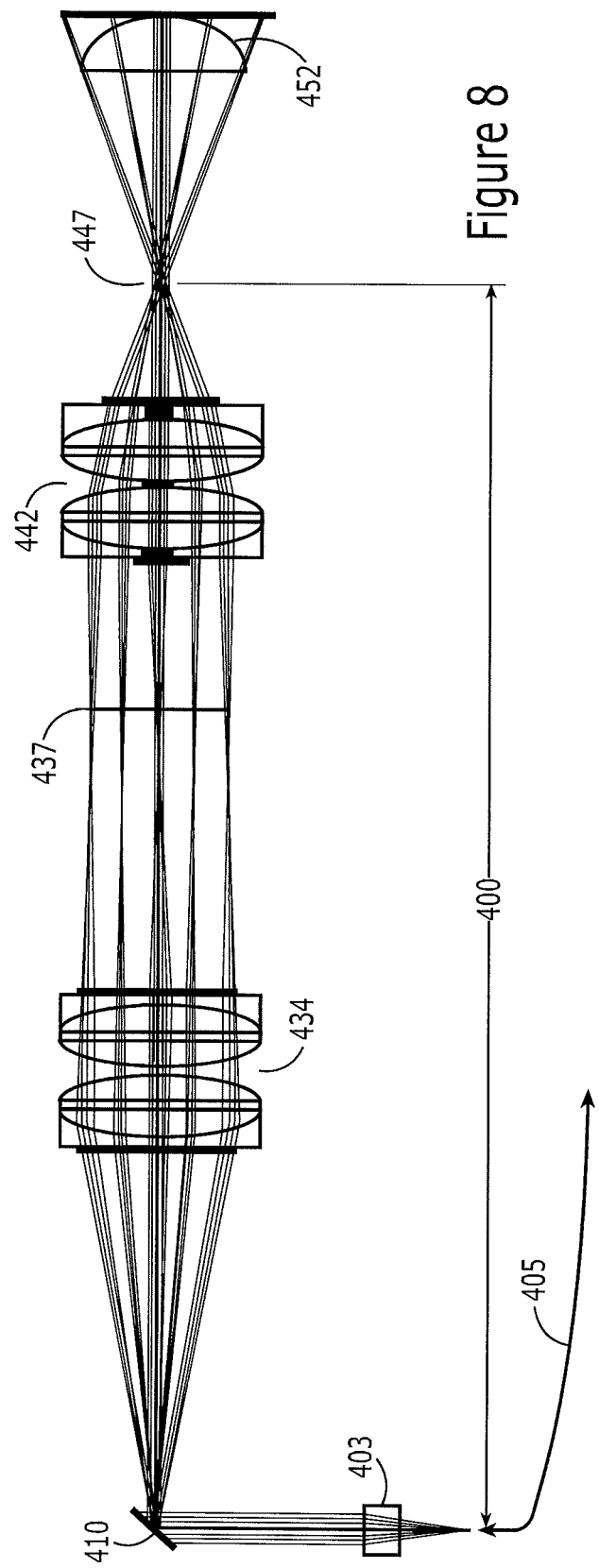
FIG. 8 is a diagram illustrating high power non-telecentric imaging optic for spherical objects in accordance with some embodiments of the present invention.
Figure 13:
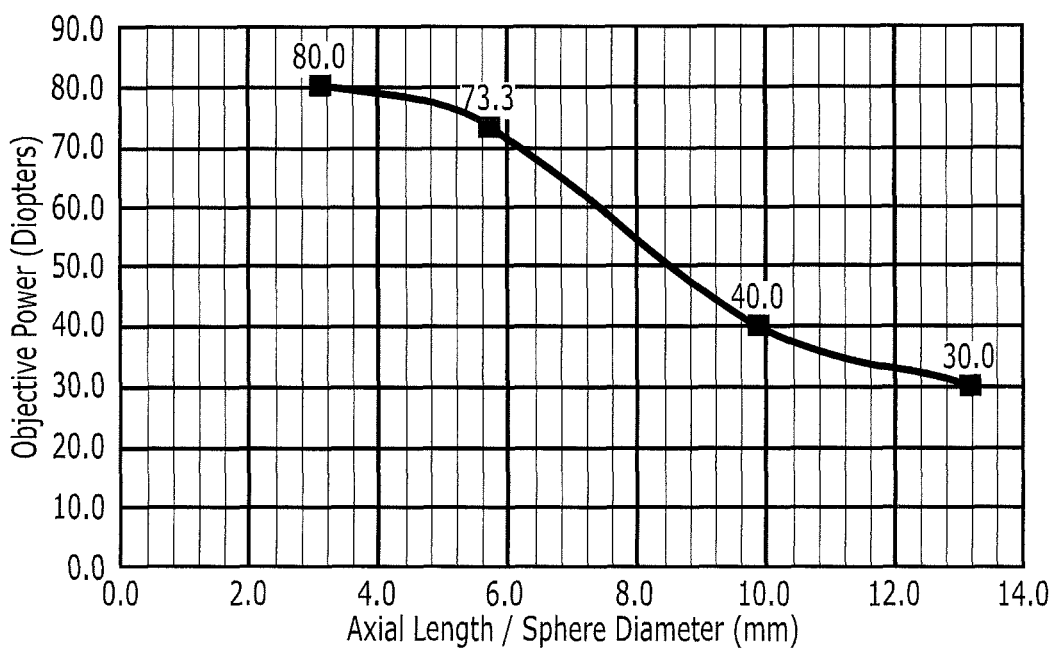
FIG. 13 is a graph illustrating Objective Power vs. Axial Length/Sphere Diameter in accordance with some embodiments of the present invention.

A solution to imaging the ball-lens phenotype of the rodent eye in accordance with some embodiments of the present invention is illustrated in FIG. 8. The basic elements are shared in common with the human imaging system: collimator, scanning galvos, telecentric lens, and focusing optics. The optics are substantially redesigned and optimized for imaging through spherical media. The telecentric lens 434 is a doublet pair, creating a telecentric plane with a substantially flattened field curvature at the telecentric plane 435. This doublet pair consists of two 100 mm focal length lenses, and yields a telecentric plane with a field curvature radius of 103 mm, as compared to the field curvature of a single achromat lens in a similar configuration of 16 mm. The focusing lens set 442 is pre-set to have substantially greater power in order to accommodate the ball-lens of the subject. For the mouse, two 25 mm focal length achromats are set for nominal power of +80 D. The separation between the galvos 410 and the proximal doublet pair 434 is 50 mm. The proximal doublet pair is separated from the distal doublet pair 442 by 65 mm. For the rat, with an eye diameter of 6.4 mm, the nominal power of the lens set 442 is 73.3 Diopters. The nominal design power scales inversely with lens diameter, owing to the curvature of the anterior surface that controls the bulk of the imaging power of the subject. The graph in FIG. 13 of objective power vs. Axial length/sphere diameter illustrates the nominal design power as a function of optical axial length.

Figure 9:
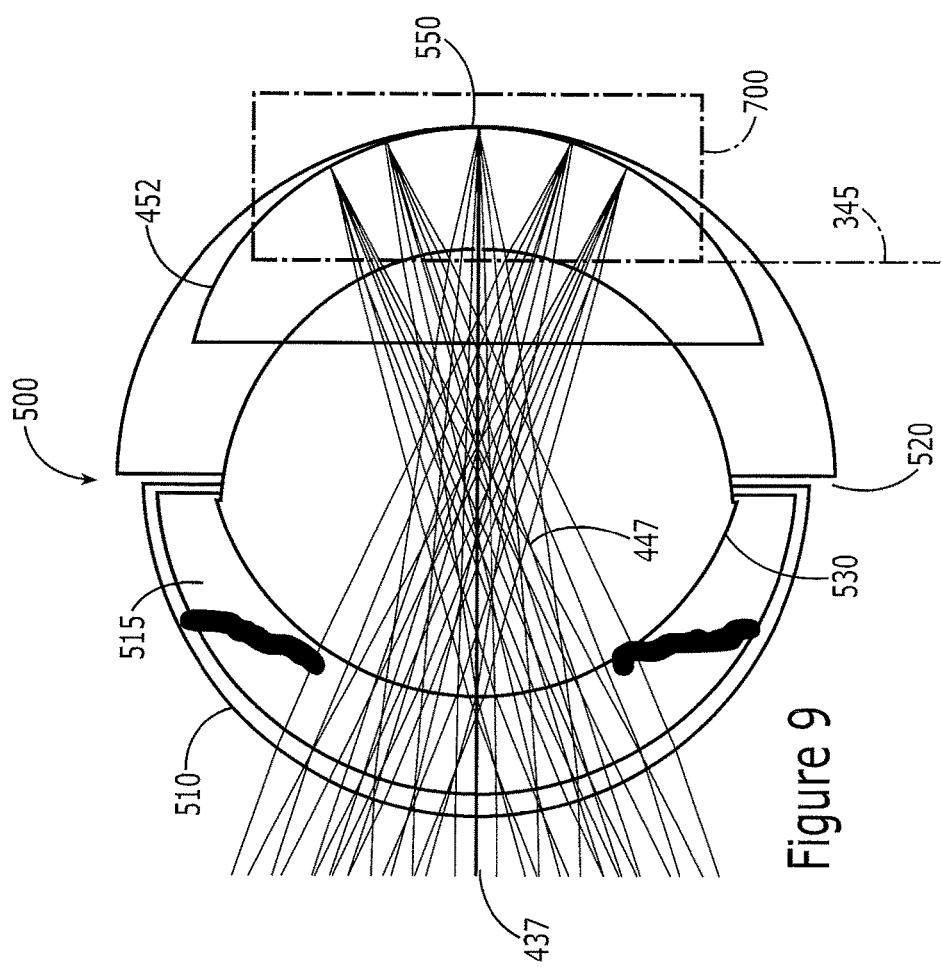
FIG. 9 is a diagram illustrating focal field curvature optimization to posterior pole radius of curvature of spherical eye in accordance with some embodiments of the present invention.
Figure 12:
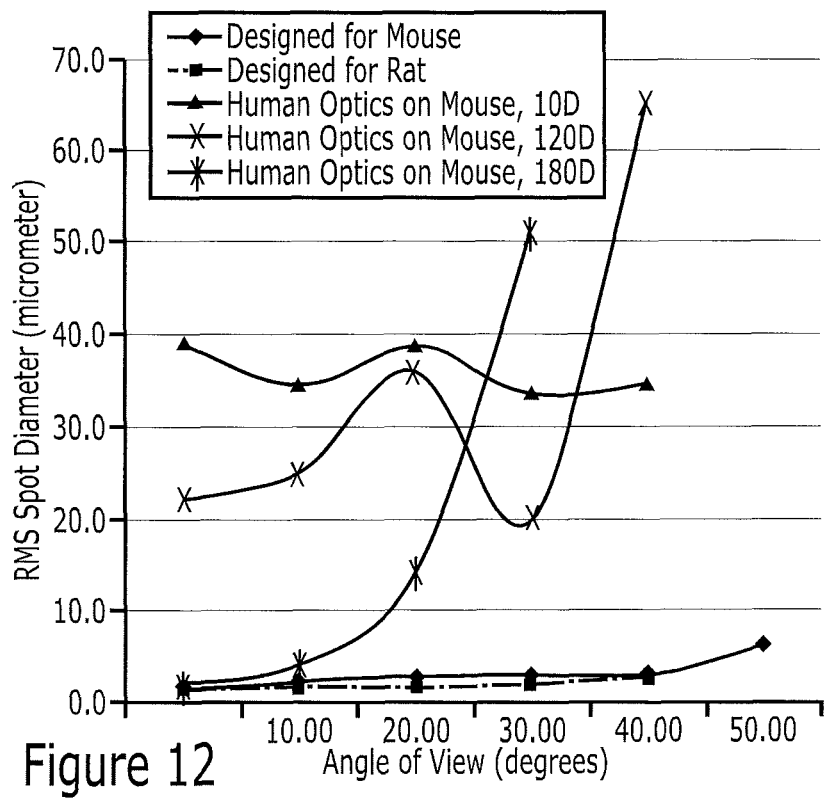
FIG. 12 is graph illustrating RMS spot size vs. angular field of view in accordance with some embodiments of the present invention.

Imaging capability of systems in accordance with some embodiments of the present invention in the mouse eye is demonstrated in FIG. 9. Referring to FIG. 9, the input rays 437 are focused at the retinal plane 550, with a field curvature described by surface 452. The focal field curvature in this case is 1.35 mm, which compares favorably with the retinal radius of curvature 1.64 mm. The on-axis rms spot size is 1.2 μm. The graph of FIG. 12 shows the rms spot size as a function of scan angle, demonstrating a 50 degree field of view. The OCT imaging window is defined by matching the reference arm path length to an effective optical path length equivalent to the distance to a chosen surface anterior to the retina 345, and described by a FDOCT window 700. It is known in the art that it may be desirable to invert the imaging window, placing the path-matching position 345 posterior to the retina; this may be done without loss of generality. Furthermore, the optical system specifics given here for mouse models may be generalized to other rodent models or any other subject that is reasonably modeled as a ball-lens optical system without loss of generality. The specific optical design prescription for the mouse model imaging is tabulated in Table 1 set out in FIG. 16.

The pre-focusing attribute of imaging systems in accordance with some embodiments of the present invention has advantages over the representative adult eye imaging system. In particular, systems in accordance with some embodiments of the present invention allow imaging of all structures of the subject eye from anterior cornea through to the posterior retina without changing lenses by controlling the working distance between the imaging system and the eye and by coordinating the path length matching condition by adjusting the reference arm path length.

Figure 10A:
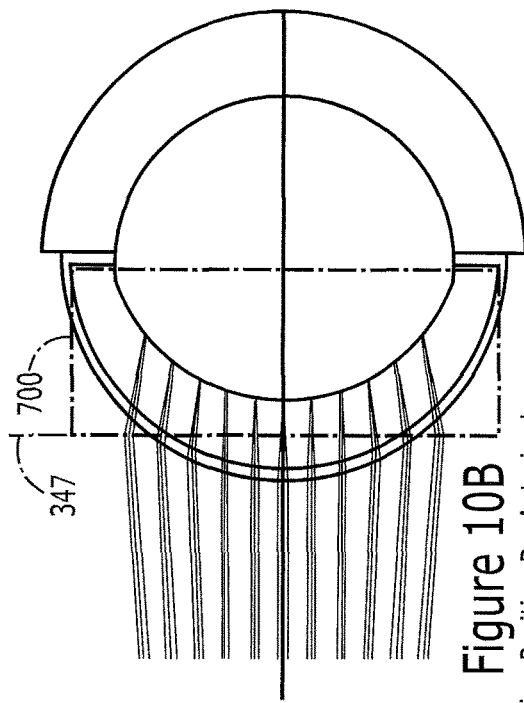
FIGS. 10A through 10D illustrate sequential imaging with systems in accordance with some embodiments of the present invention from the cornea to the retina.
Figure 10B:
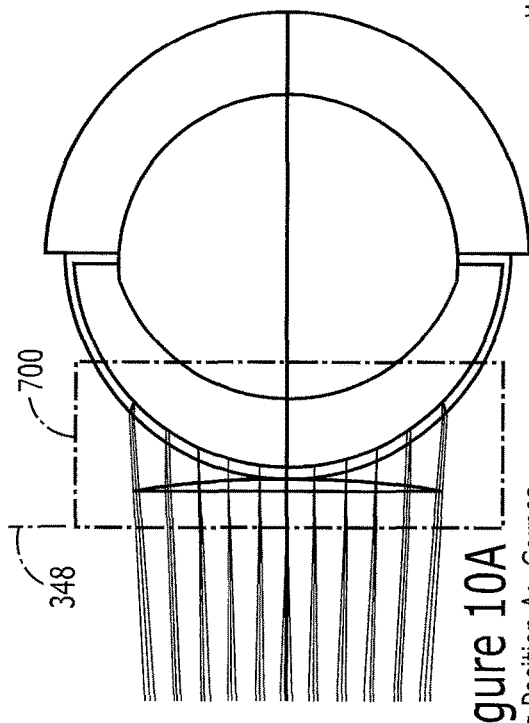
Figure 10C:
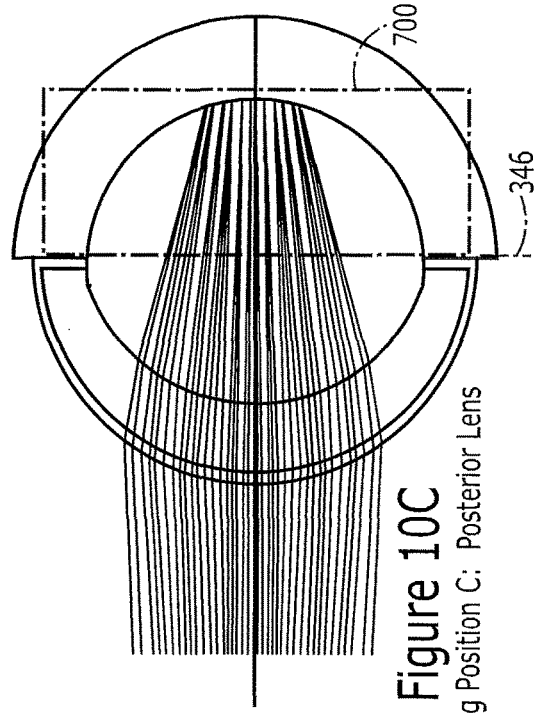
Figure 10D:
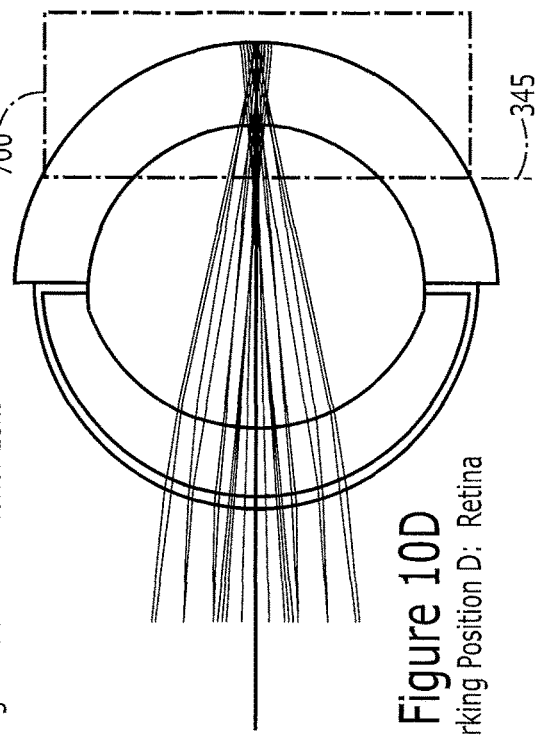

FIGS. 10A through 10D illustrate sequential imaging with systems in accordance with some embodiments of the present invention from the cornea to the retina. As illustrated in FIG. 10A, the system is focused on the cornea, with the path length match position 348. As the working distance is reduced, the focus is translated to the anterior of the ocular lens, with the path length position 347 illustrated in FIG. 10B. The working distance is further reduced to image the posterior lens, as shown in FIG. 10C, with the path length match position at 346. Finally, the retina is imaged in FIG. 10D, with path length match condition 345. The relative optical path length vs. imaging position is illustrated in a graph in FIG. 14.

The optimum position for imaging any structure in the eye is a function of focus, location of the focus relative to a surface, and location of the reference path matching position to the focus. Optical systems in accordance with some embodiments of the present invention are optimized for the retina, in the sense that the field curvature at the retina matches the curvature of the retina. The field curvature does not match that of the all the other ocular structures, so it is desirable to set the imaging conditions for optimum imaging of the desired structure. Most notably, it is often desirable to have high resolution, lateral and axial, images of the cornea. Axial resolution in OCT is primarily a function of the source bandwidth and not the delivery optics, but axial resolution may be impaired when lateral resolution is poor, as the interferometric signal is intensity-weighted over the lateral spot. Accordingly, it may be useful to position the focus for optimal lateral resolution.

Figure 11B:
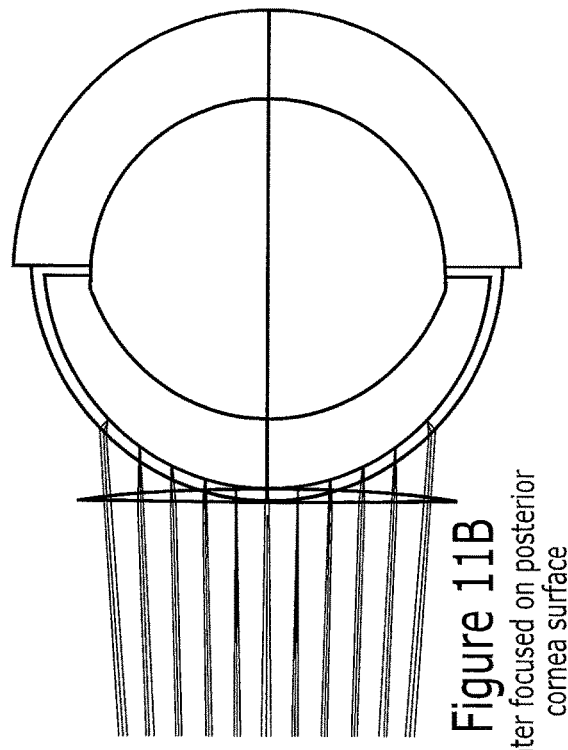
FIGS. 11A through 11C illustrate positions for imaging cornea for lateral resolution in accordance with some embodiments of the present invention.
Figure 11A:
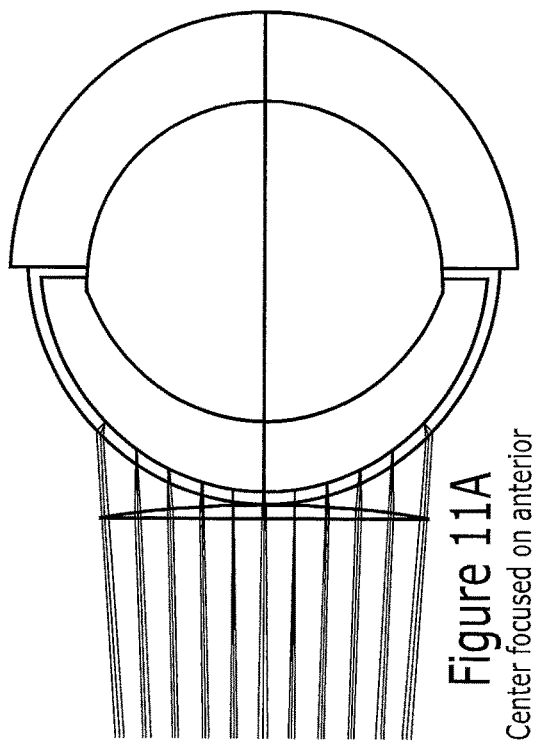
Figure 11C:
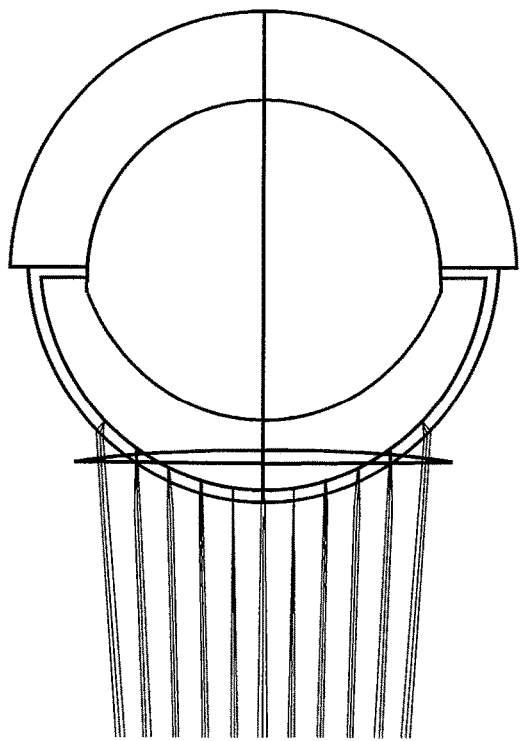

FIGS. 11A through 11C illustrate various positions for focal placement to image the cornea. The field curvature of the optical system is inverted with respect to that of the cornea, as, in fact, the rays are divergent as they enter the cornea. Three locations for focal placement are at the anterior surface of the cornea (FIG. 11A); posterior surface of the cornea (FIG. 11B); and posterior to the cornea (FIG. 11C). The optimal on-axis lateral resolution is achieved by placing the focal position at the anterior surface or posterior surface for concentration on these surfaces, respectively. The optimal uniformity of lateral resolution across a field of view is achieved by placing the focus posterior to the cornea.

Figure 14:
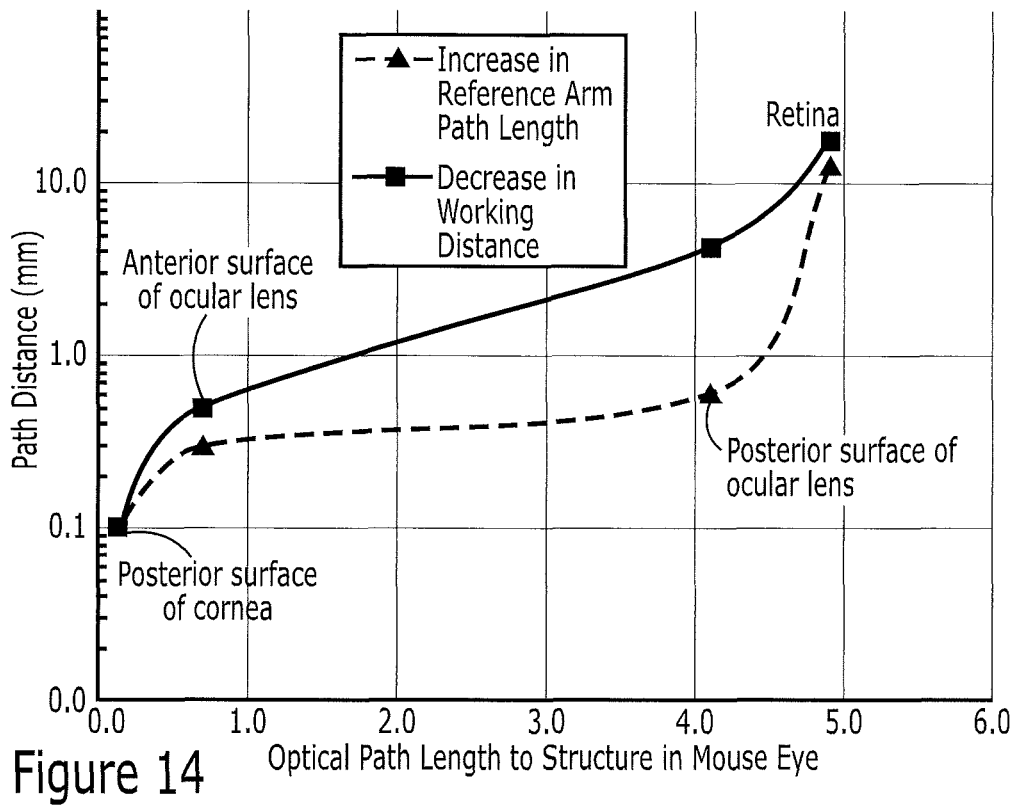
FIG. 14 is a graph illustrating Path Length Increase vs. Working Distance Decrease Corresponding to Imaging structures from Anterior to Posterior in accordance with some embodiments of the present invention.
Figure 15:
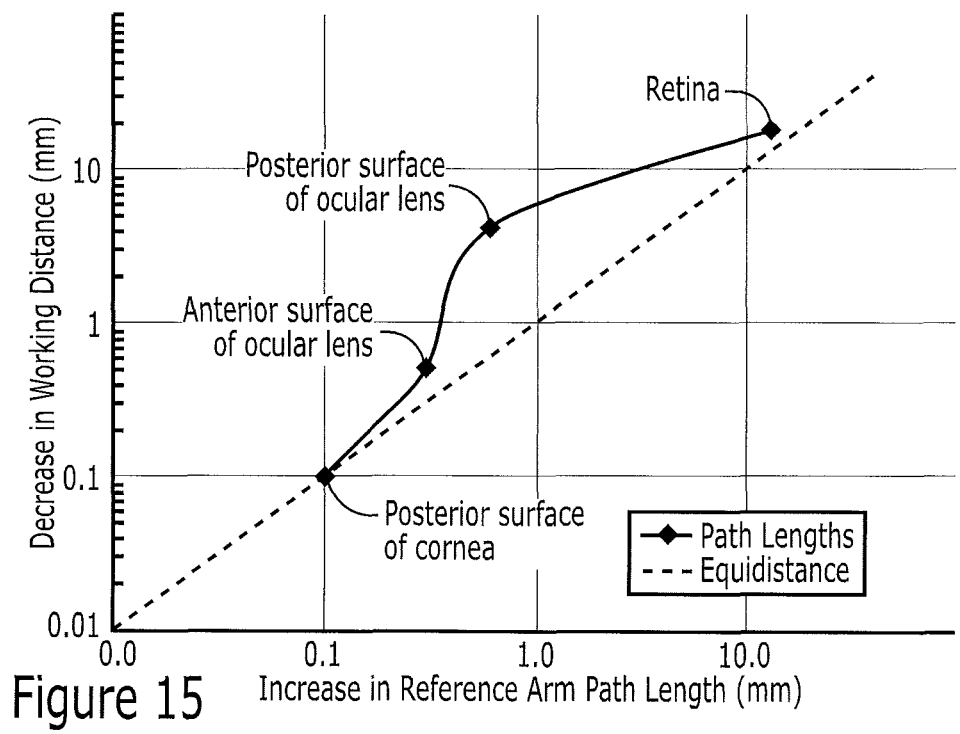
FIG. 15 is a graph illustrating Path Length Increase vs. Working Distance Decrease Corresponding to Imaging structures from Anterior to Posterior in accordance with some embodiments of the present invention.

In all of the cases illustrated in FIGS. 11A through 11C, from optimizing the imaging of the cornea to imaging any structure through to the retina, it is desirable to optimize the reference arm to maintain the path-matching condition. Optical systems in accordance with some embodiments of the present invention not only provide optimal imaging of spherical ocular systems, but uniquely enable automated sequential whole-eye imaging in a series of volumetric slices. The system may readily be set to image on the anterior-most surface, with appropriate focus, working distance, and reference arm position. The relationship between working distance decrease and reference arm path length increase is non-linear, as shown in FIGS. 14 and 15. The acquisition may then be automated to collect a series of whole-body volumes without manual intervention by simply coordinating the reduction in working distance with the reference arm length according to a functional relationship or look-up table as described above. At current image acquisition speeds of 20,000 lines per second, high density images of 512×512×512 pixels may be acquired, processed and displayed in 13 seconds. A mouse or rat eye may be imaged in 3 sequential volumes offset by 1-2 mm (subject dependent) with significant content overlap in 40 seconds; the content overlap enabling volume registration and image stitching. In some embodiments, lower density images of 256×256×512 pixels may be imaged in 3 seconds, with 3 sequential volumes acquired in 12 seconds. With emerging devices, imaging speeds will most likely rapidly increase to 100,000 lines per second or faster, enabling high density, high resolution anterior-to-posterior volumes in under 10 seconds for dramatic high-throughput high resolution imaging of ocular structures from cornea to retina in one image.

Example functionality of systems in accordance with some embodiments of the present invention will now be discussed herein. In order to view the retina, the operator moves the handheld probe (portable OCT system) and lens bore closer to the eye of the patient, using the OCT image to guide the process. Some embodiments of the present invention provide a scanning OCT probe which is "easy to drive" in that the operator can clearly see major intermediate structures, for example, ocular structures-such as the cornea, iris, crystalline lens, and finally the retina as he "drives" in toward the object of interest. In contrast to the fixed lens system described above, a variable system offers certain improved imaging attributes for optimizing anterior imaging and subsequently optimizing posterior imaging. This is achieved by controlling certain optical distances in the system by extending or contracting the probe bore.

OCT systems have been designed, manufactured and deployed for diagnosis of eye disease in patient populations with refractive errors ranging from myopia or nearsightedness, to emmetropia or no refractive error, to hyperopia or farsightedness. The greatest difficulty in using OCT systems clinically is often the difficulty the operator has in obtaining a high quality image of the structure of interest, which may be the retina, for example, in patients with macular degeneration or glaucoma, the iris and crystalline lens, for example, in patients with cataract or other lens defects, or the cornea, for example, in refractive surgery patients. Much of the intuition one develops in using "standard camera" (noninterferometric) optics, breaks down or is incomplete when using interferometrically based optical systems, such as OCT. In particular, the need to simultaneously achieve both good optical focus and appropriate reference arms length as the operator is searching for visible landmarks in the eye can be daunting. Some embodiments of the present invention separate changes in focus from changes in optical path length, which determines the reference arm length required. This may greatly simplify the use of the portable OCT systems (handheld probe) in accordance with some embodiments of the present invention.

Figure 17A:
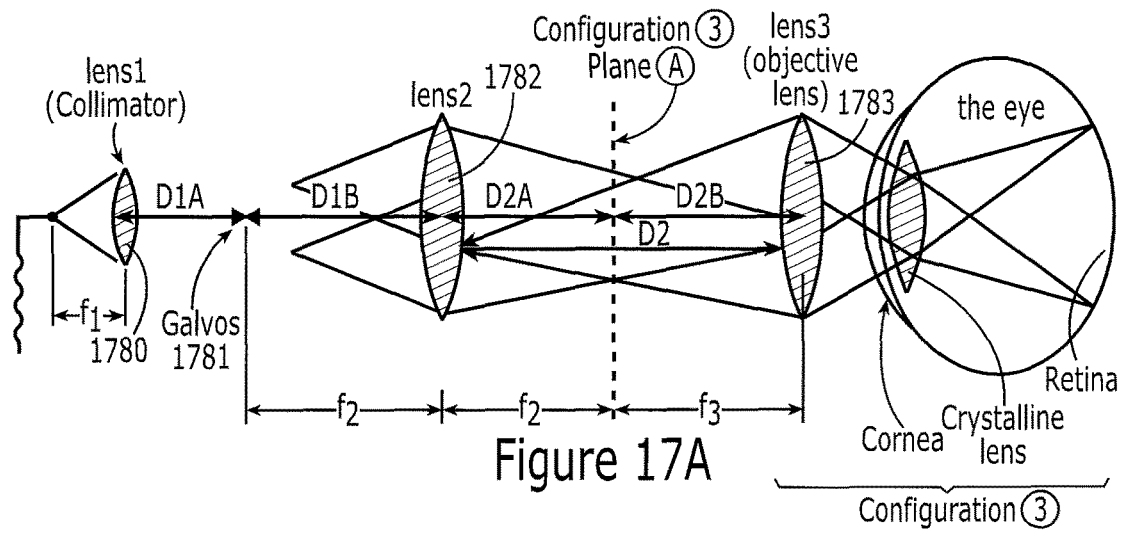
FIGS. 17A through 17C are diagrams illustrating three lens complexes including in OCT systems in accordance with some embodiments of the present invention.
Figure 17B:
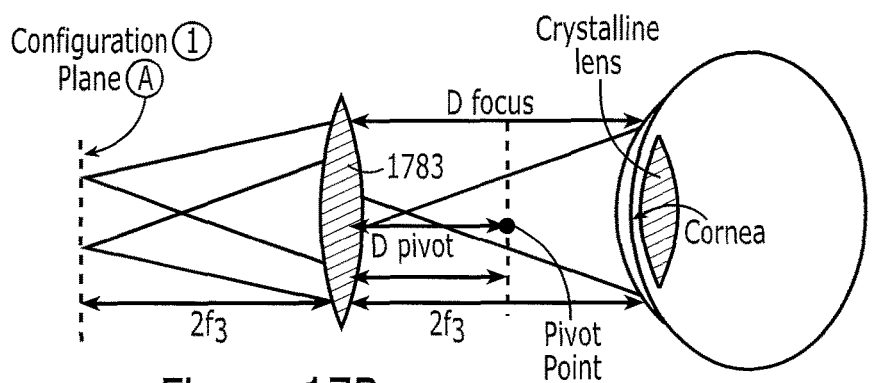
Figure 17C:
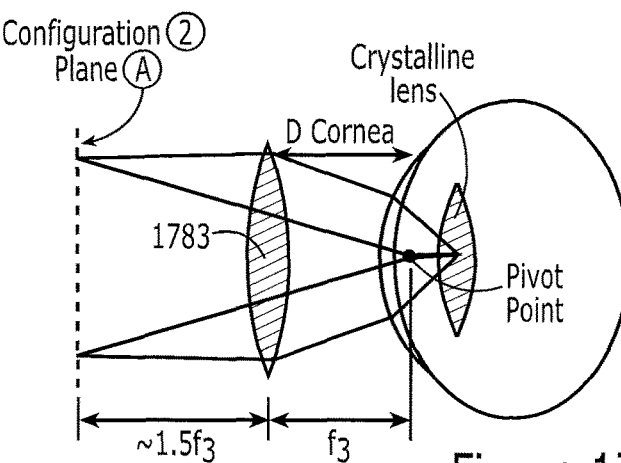

In particular, OCT systems in accordance with some embodiments of the present invention have three lens complexes, each of which may be made up of one or more lenses. Three lens complexes according to some embodiments of the present invention are illustrated in FIGS. 17A through 17C. Referring first to FIG. 17A, from left to right, the first lens 1780 is called the collimator lens with focal length f1. At a distance D1A to the right of the collimator lens 1780 are a galvanometer or galvanometer pair (galvos) 1781 which steer (or scan) the light beam over the region of interest. Assuming the light is well collimated, the distance D1A is a free parameter whose value does not typically affect the geometrical optical performance of the system and, may thus be governed by other considerations such as mechanical constraints or control of the optical path length through the system. At a distance D1B=f2 from the galvanometers(s) is the second lens 1782 with focal length f2. A distance D2A=f2 to the right of the second lens 1782 is a plane Plane A perpendicular to the optical axis dividing the distance D2 into two parts: D2A, which is approximately equal to f2, and D2B which is variable. In each of the configurations discussed below, the system to the left of Plane A is unchanged, i.e. D1A may be freely adjusted, and D1B and D2A are kept constant at f2. The third lens 1783 called the objective lens has a focal length f3 and is a variable distance D2B to the right of Plane A. To the right of the objective lens 1783 in the "open air", i.e. outside the bore, are several distances of interest. The distance from the objective lens 1783 to the anterior surface of the cornea D_cornea, the distance to the "pivot point" D_pivot at a point optically conjugate to the position of the galvanometers 1781, where the scanning beams cross, and the distance, in air, i.e. not affected by the optics of the eye, D_focus where the optical beams are in focus.

Using a first order analysis; second and higher order effects due to aberrations, for example, small changes in D_pivot and D_focus due to changes in D2B will be ignored. To first order, distance D_pivot will be approximately f3 beyond lens 3, and distance D_focus can be determined by the following lens formula:

$$1/D2B + 1/D\_focus = 1/f3 \qquad \text{Equation 1}$$

This formula assumes that the index of refraction of the media in which D2B and D_focus reside is equal to 1, i.e. in air.

Operations of a portable OCT system (handheld probe in accordance with some embodiments of the present invention will be discussed with respect to FIGS. 17A through 17C. Referring first to FIG. 17B (configuration 1), to begin imaging the eye, the operator extends the probe bore tip containing the objective lens 1783 by, for example, clockwise (CW) or counter clockwise (CCW) twisting or linear braked friction extension, or other control to a hard stop, which increases the distance D2B to a threshold or maximum value. This value can be determined based on the lens formula set out in Equation D1 above to place D_focus at a convenient distance from lens 3 or objective lens 1783 for imaging the cornea and also to optimize the depth of focus to a desired value which is appropriate for the cornea. As illustrated in FIG. 17B, setting D2B=2*f3, for example, sets D_focus=2*f3 as well. This nominal "cornea" setting is appropriate for viewing the anterior surface of the cornea or any other structure whose surface is to be examined in air, after which the operator will be ready to "drive" the handheld probe inward to visualize deeper structures as discussed further below.

Referring now to FIG. 17C (configuration 2), as the operator drives the probe inward, i.e. moves the handheld probe and lens closer to the eye of the patient, the operator slowly draws the probe bore tip toward the nominal "lens" position, which shortens D2B and lengthens D_focus, while D_pivot remains constant. However, the optical power of the cornea now adds additional positive focusing power which shortens the physical distance to the focus until it is located approximately at the iris and crystalline lens of the eye. This corresponds to D2B between f3 and 2*f3, for example, 1.5*f3 as illustrated in FIG. 17C. At this point, the anterior segment of the eye, particularly the cornea, provides part of the optical power required to focus the optical beam on the intermediate structures, such as the iris and crystalline lens.

Referring again to FIG. 17A (configuration 3), this is the configuration for collecting images of the retina. As the operator moves the probe closer to the eye, the operator also contracts the probe bore tip back all the way to the nominal "retina" position, which occurs when D2B=f3, and continues moving in until D_cornea equals the design working distance to the eye and D_pivot places the pivot point in the iris plane so that it will be minimally vignetted while the focus scans over the surface of the retina. This position setting can also incorporate some additional adjustment providing additional excursion in D2B to accommodate a range of refractive errors in subjects. For example, when D2B is approaching, but still greater than f3, the scanning beam exiting lens f3 will still be converging and will thus focus correctly on the retina in eyes which are too short, or hyperopic. This is the appropriate setting for mice which tend to have severely hyperopic eyes. When D2B=f3, this is the correct setting for emmetropic eyes. By allowing D2B to be adjusted to values less than f3, this will accommodate myopic eyes. Calibrated diopter settings can be labeled or engraved on the probe bore so that accurate diopter values can be dialed in for subjects with known refractive error.

A major benefit of handheld probes in accordance with some embodiments of the present invention is that it is at least partly self compensating_ in optical path length, i.e. as the probe is advanced from corneal to lens to retinal focus, the probe itself is shortened as D2B ranges from D2B=~2*f3, to f3<D2B<2*f3, to D2B=~f3, thus the decreasing optical path length of the probe is compensated by the increasing pathlength in the media of the eye, so that the overall optical path length may be designed to be relatively constant during this process. This is of great benefit in OCT, where changes in the optical path length of the sample probe can cause instabilities in the position of the OCT image in the available depth viewing range. In fact this condition of zero path length variation can be taken as a design parameter to optimize the range over which D2B can be adjusted. In some embodiments, if this is not practical or desired, alternative means may be provided for adjusting the optical path length of other segments of the sample or reference arm, such as changing distance D1A in the probe or changing the reference arm length via standard means, to allow for maintenance of constant optical path length difference between the arms as the probe bore is extended and contracted. This can be done by, for example, monitoring the position of the probe bore through a mechanical displacement or rotation sensor, using image processing to monitor the position of some feature of the OCT image in axial length, or through other means without departing from the scope of the present invention.

Thus, according to some embodiments of the present invention is may be much easier to obtain high resolution depth-resolved images of retinal and other ocular pathologies over a broad field of view in patients with a wide range of refractive errors and a wide range of ocular axial lengths. Finally, since the accommodative state of the lens may change during the exam, which is largely independent of axial length, there is a need to easily correct focus independent of reference arm length.

As discussed above, some aspects of the present invention may be implemented by a data processing system. Exemplary embodiments of a data processing system 1830 configured in accordance with embodiments of the present invention will be discussed with respect to FIG. 18. The data processing system 1830 may include a user interface 1844, including, for example, input device(s) such as a keyboard or keypad, a display, a speaker and/or microphone, and a memory 1836 that communicate with a processor 1838. The data processing system 1830 may further include I/O data port(s) 1846 that also communicates with the processor 1838. The I/O data ports 1846 can be used to transfer information between the data processing system 1830 and another computer system or a network using, for example, an Internet Protocol (IP) connection. These components may be conventional components such as those used in many conventional data processing systems, which may be configured to operate as described herein.

Figure 19:
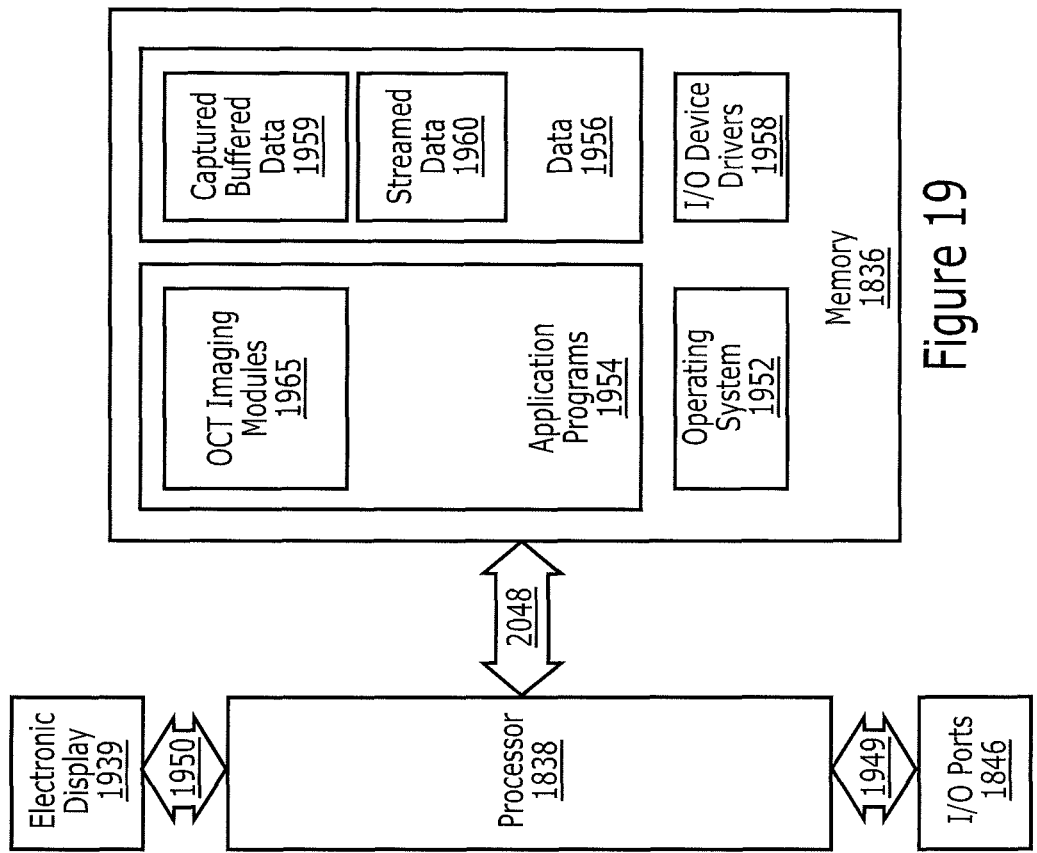
FIG. 19 is a more detailed block diagram of a system according to some embodiments of the present invention.
Figure 18:
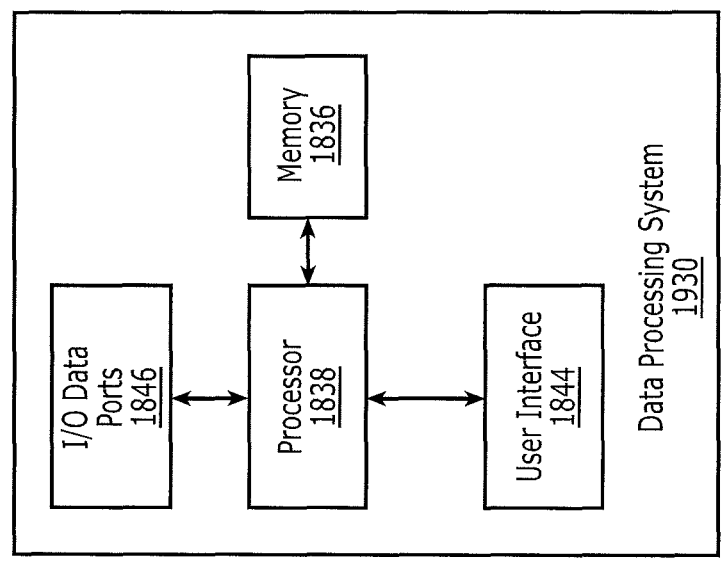
FIG. 18 is a block diagram of a data processing system suitable for use in some embodiments of the present invention.

Referring now to ', a more detailed block diagram of a data processing system of FIG. 18 is provided that illustrates systems, methods, and computer program products in accordance with some embodiments of the present invention, which will now be discussed. As illustrated in FIG. 19, the processor 1838 communicates with the memory 1836 via an address/data bus 1948, the I/O data ports 1846 via address/data bus 1949 and the electronic display 1939 via address/data bus 1950. The processor 1838 can be any commercially available or custom enterprise, application, personal, pervasive and/or embedded microprocessor, microcontroller, digital signal processor or the like. The memory 1836 may include any memory device containing the software and data used to implement the functionality of the data processing system 1830. The memory 1836 can include, but is not limited to, the following types of devices: ROM, PROM, EPROM, EEPROM, flash memory, SRAM, and DRAM.

As further illustrated in FIG. 19, the memory 1836 may include several categories of software and data used in the system: an operating system 1952; application programs 1954; input/output (I/O) device drivers 1958; and data 1956. As will be appreciated by those of skill in the art, the operating system 1952 may be any operating system suitable for use with a data processing system, such as OS/2, AIX or zOS from International Business Machines Corporation, Armonk, N.Y., Windows95, Windows98, Windows2000 or WindowsXP, or Windows CE or Windows 7 from Microsoft Corporation, Redmond, Wash., Palm OS, Symbian OS, Cisco IOS, VxWorks, Unix or Linux. The I/O device drivers 1958 typically include software routines assessed through the operating system 1952 by the application programs 1954 to communicate with devices such as the I/O data port(s) 1846 and certain memory 1836 components. The application programs 1954 are illustrative of the programs that implement the various features of the some embodiments of the present invention and may include at least one application that supports operations according to embodiments of the present invention. Finally, as illustrated, the data 1956 may include captured buffer data 1959 and streamed data 1960, which may represent the static and dynamic data used by the application programs 1954, the operating system 1952, the I/O device drivers 1958, and other software programs that may reside in the memory 1836.

As further illustrated in FIG. 19, according to some embodiments of the present invention, the application programs 1954 include OCT imaging modules 1965. While the present invention is illustrated with reference to OCT imaging modules 1965 as being application programs in FIG. 19, as will be appreciated by those of skill in the art, other configurations fall within the scope of the present invention. For example, rather than being application programs 1954, these circuits and modules may also be incorporated into the operating system 1952 or other such logical division of the data processing system. Furthermore, while the OCT imaging modules 1965 are illustrated in a single system, as will be appreciated by those of skill in the art, such functionality may be distributed across one or more systems. Thus, the present invention should not be construed as limited to the configuration illustrated in FIG. 19, but may be provided by other arrangements and/or divisions of functions between data processing systems. For example, although FIG. 19 is illustrated as having various circuits, one or more of these circuits may be combined without departing from the scope of the present invention.

It will be understood that the OCT imaging modules 1965 may be used to implement various portions of the present invention capable of being performed by a data processing system. For example, the OCT imaging modules may be used to process and assess the images produced by the OCT system according to some embodiments of the present invention.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed exemplary embodiments of the invention. However, many variations and modifications can be made to these embodiments without substantially departing from the principles of the present invention. Accordingly, although specific terms are used, they are used in a generic and descriptive sense only and not for purposes of limitation, the scope of the invention being defined by the following claims.

That which is claimed is:

1. A scanning optical imaging system for imaging structures adjacent a posterior surface of a substantially spherical ball-lens device, the system comprising:
    a source of optical radiation having an associated source arm path;
    a sample arm having an associated sample arm path coupled to the source arm path, the sample arm delivering optical radiation from an output of the source to a first optical subsystem following the output of the source, at least one scanning mirror following the first optical subsystem, at least one optical element following the at least one scanning mirror, and the substantially spherical ball lens device following the at least one optical element;
    a non-zero working distance between the at least one optical element and the substantially spherical ball lens device,
    wherein the working distance between the at least one optical element and the substantially spherical ball lens device are configured to adjust such that a conjugate of the at least one scanning mirror is imaged interior to the substantially spherical ball lens device, posterior to an anterior surface of the substantially spherical ball lens device and anterior to the posterior surface of the substantially spherical ball lens device; and
    wherein the optical radiation from the output of the source is focused to an intermediate conjugate anterior to the substantially spherical ball lens device, wherefrom the intermediate conjugate of the optical radiation from the output of the source is focused to a region posterior to an image of the at least one scanning mirror and to a region adjacent the posterior surface of the substantially spherical ball lens device,
    wherein structures adjacent the posterior surface of the substantially spherical ball lens device include the subject under test.

2. The scanning optical imaging system of claim 1, wherein the optical radiation from the output of the source is focused to a substantially telecentric intermediate conjugate.

3. The scanning optical imaging system of claim 1:
    wherein the at least one optical element within the sample arm has adjustable optical focusing power; and
    wherein the adjustable optical focusing power is controlled to adjust a position of focus relative to the posterior surface of the substantially spherical ball lens device.

4. The scanning optical imaging system of claim 1:
    wherein the at least one optical element within the sample arm has adjustable optical focusing power; and
    wherein the adjustable optical focusing power is controlled to adjust a position of focus relative to the posterior surface of the substantially spherical ball lens device dependent on a diameter of the substantially spherical ball lens device.

5. The scanning optical imaging system of claim 1:
    wherein the at least one optical element within the sample arm comprises at least one interchangeable element configured to adjust optical focusing power; and
    wherein the at least one interchangeable element is selected to adjust a position of focus relative to the posterior surface of the substantially spherical ball lens device dependent on a diameter of the substantially spherical ball lens device.

6. The scanning optical imaging system of claim 1, wherein the substantially spherical ball lens device is a distal optical element in the sample arm of the imaging system.

7. The scanning optical imaging system of claim 6, wherein the sample arm with the substantially spherical ball lens device is positioned proximate a subject under test.

8. The scanning optical imaging system of claim 1, wherein the substantially spherical ball lens device is an element physically separate from the sample arm of the imaging system.

9. The scanning optical imaging system of claim 8, wherein the substantially spherical ball lens device is proximate a subject under test.

10. The scanning optical imaging system of claim 8, wherein the substantially spherical ball lens device is a subject under test.

* * * * *